US007666412B2

(12) United States Patent
Thompson

(10) Patent No.: US 7,666,412 B2
(45) Date of Patent: Feb. 23, 2010

(54) METHODS FOR THE TREATMENT OF NEOPLASTIC DISORDERS WITH ANTI-CAVEOLIN AGENTS

(75) Inventor: Timothy C. Thompson, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 982 days.

(21) Appl. No.: 10/690,713

(22) Filed: Oct. 22, 2003

(65) Prior Publication Data
US 2005/0036986 A1 Feb. 17, 2005

Related U.S. Application Data

(63) Continuation of application No. 10/151,055, filed on May 21, 2002, now abandoned, which is a continuation of application No. 09/797,969, filed on Mar. 5, 2001, now Pat. No. 7,029,859, which is a continuation of application No. 09/186,184, filed on Nov. 5, 1998, now Pat. No. 6,252,058.

(60) Provisional application No. 60/064,351, filed on Nov. 5, 1997.

(51) Int. Cl.
A61K 39/395 (2006.01)
(52) U.S. Cl. ............... 424/130.1; 424/155.1; 424/141.1
(58) Field of Classification Search .................... None
See application file for complete search history.

(56) References Cited

U.S. PATENT DOCUMENTS

| 4,317,818 | A | 3/1982 | Benson et al. |
| 4,925,835 | A | 5/1990 | Heston |
| 5,116,615 | A | 5/1992 | Gokcen et al. |
| 5,260,224 | A | 11/1993 | Stossel et al. |
| 5,633,161 | A | 5/1997 | Shyjan |
| 5,783,182 | A | 7/1998 | Thompson |
| 5,834,234 | A | 11/1998 | Gallo |

FOREIGN PATENT DOCUMENTS

| WO | WO 86/03226 | 6/1986 |
| WO | WO 94/04196 | 3/1994 |
| WO | WO 94/16737 | 8/1994 |
| WO | WO 94/28129 | 12/1994 |
| WO | WO 95/19369 | 7/1995 |
| WO | WO 96/30389 | 10/1996 |
| WO | WO 97/09055 | 3/1997 |
| WO | WO 97/18454 | 5/1997 |
| WO | WO 99/22773 | 5/1999 |

OTHER PUBLICATIONS

Jain R. K. Scientific American, 271(1): 58-65, Jul. 1994.*
Dillman R. O., Annals of Internal Medicine, 111:592-603, 1989.*
Weiner L. M. Seminars in Oncology, 26 (4 Suppl 12): 41-50, Aug. 1999.*
Dillman, R. O. Journal of Clinical Oncology, 12(7):1497-1515, 1994.*
Nelson, J. B. Nature Medicine, 4:1011-1012, 1998.*
Lee et al., Oncogene, vol. 16, p. 1391-1397, 1998.*
Yang et al Clinical Cancer Research vol. 4, p. 1873-80, Aug. 1998. IDS: HHH.*
Meredith et al Prostate Carcinoma Radioimmunotherapy, vol. 35 p. 1017-1022. 1994.*
Goethuys et al. Am J Clin Oncol. vol. 20, p. 40-5, 1997.*
Nasu et al. Nat Med, vol. 4, p. 1062-3, Sep. 1998.*
Welch, Danny R., et al. "Transforming growth factor β stimulates mammary adenocarcinoma cell invasion and metastatic potential", Proc. Natl. Acad. Sci. USA, vol. 87, pp. 7678-7682. Oct. 1990.
Thompson, Timothy C., et al. "Multistage Carcinogenesis Induced by ras and myc Oncogenes in a Reconstituted Organ", Cell, vol. 56, pp. 917-930. Mar. 24, 1989.
Fingert et al., "In vivo model for differentiation therapy of leukemia and solid tumors." National Institutes of Health Publication, 84-2635, Serno Symposia Publications from Rven. Press, pp. 277-286 (1984).
Taber's Cyclopedic Medical Dictionary, F.A. David Company, Philadelphia, PA, edited by Vardara et al. (1993).
Liang, Peng, et al., "Differential Display and Cloning of Messenger RNAs from Human Breast Cancer versus Mammary Epithelial Cells", Cancer Research, 52, pp. 6966-6968. Dec. 15, 1992.
Merz, et al. "Elevated Transforming Growth Factor-β1 and β3 mRNA Levels are Associated with ras+myc-Induced Carcinomas in Reconstituted Mouse Prostate: Evidenced for a Paracrine Role during Progression". Molecular Endocrinology, vol. 5, No. 4, (1991) pp. 503-513.
Poster Session Abstracts: First SPORE Investigators' Meeting, "The Role of Retinoids in Prostate Cancer Chemoprevention" Jul. 18-20, 1993, p. 30.
Slawin, et al. "Dietary Fenretinide, a Synthetic Retinoid, Decreases the Tumor Incidence and the Tumor Mass of ras+myc-induced Carcinomas in the Mouse Prostate Reconsititution Model System", Cancer Research, vol. 53, pp. 4461-4465, Oct. 1, 1993.
Thompson, et al. "Transgenic Models for the Study of Prostate Cancer", (Supplement) Cancer, vol. 71, No. 3, Feb. 1, 1993, pp. 1165-1171.
Donehower, et al. "Mice deficient for p53 are developmentally normal but susceptible to spontaneous tumours", Articles, Nature, vol. 356, Mar. 19, 1992, pp. 215-221.
Thompson, et al.,"Loss of p53 function leads to metastasis in ras+myc-initiated mouse prostate cancer", Oncogene (1995) vol. 10, pp. 869-879.

(Continued)

Primary Examiner—Larry R. Helms
Assistant Examiner—Lei Yao
(74) Attorney, Agent, or Firm—Vinson & Elkins LLP

(57) ABSTRACT

The present invention relates to methods for the diagnosis, evaluation and treatment of metastatic diseases using metastatic sequences, such as caveolin, to target metastatic cells. According to the methods of the present invention, certain cancers, including metastatic prostate cancer, may be treated by therapies which suppress expression of the caveolin gene. The present invention relates to biological technologies designed to block the activity of caveolin or the function of caveolae, including vector delivery of antisense caveolin sequences, the use of anti-caveolin antibodies, the use of promoters, and other approaches targeting the expression of caveolin.

7 Claims, 6 Drawing Sheets

OTHER PUBLICATIONS

Macoska, et al. "Loss of the 17p Chromosomal Region in a Metastatic Carcinoma of the Prostate", *The Journal of Urology*, vol. 147, Apr. 1992, pp. 1142-1146.

Taylor, et al. "Evidence for synergistic interactions between ras, myc and a mutant form of p53 in cellular transformation and tumor dissemination", *Oncogene*, Feb. 10, 1992, pp. 1383-1390.

Hall, et al. "Adenylate Kinase: An Oncodevelopmental Marker in an Animal Model for Human Prostatic Cancer", *Clinical Chemistry*, vol. 31, No. 10, (1985), pp. 1689-1691.

Thompson, et al., Multistage Carcinogenesis Induced by ras and myc Oncogenes in a Reconstituted Organ, *Cell*, vol. 56, pp. 917-930, Mar. 24, 1989.

Slawin, et al., American Urological Association, Inc., Annual Meeting—San Antonio, Oct. 1, 1992, Dietary Retinoids Decrease the Incidence and Increase Lymphocytic Infiltration of ras+myc Induced Carcinomas in the Mouse Prostate Reconstitution Model System.

Thompson, et al.. "Transforming Growth Factor $\beta1$ as a Biomarker for Prostate Cancer", *Journal of Cellular Biochemistry*, Supplement 16H: pp. 54-61 (1992).

Thompson et al. "Genetic Predisposition and Mesenchymal-Epithelial Interactions in ras+myc-Induced Carcinogenesis in Reconstituted Mouse Prostate" *Molecular Carcinogenesis*, vol. 7, pp. 165-179 (1993).

Bookstein et al. "p53 Is Mutated in a Subset of Advanced-Stage Prostate Cancer[1]", *Cancer*, vol. 53, pp. 3369-3373, Jul. 19, 1993.

Carter, et al. "Prediction of Metastatic Potential in an Animal Model of Prostate Cancer: Flow Cytometric Quantification of Cell Surface Charge", *The Journal of Urology*, vol. 142, pp. 1338-1341, Nov. 1989.

Fox, et al. "p53 And c-myc Expression in Stage A1 Prostatic Adenocarcinoma: Useful Prognostic Determinants?" *The Journal of Urology*, vol. 150, pp. 490-494, Aug. 1993.

Einstein, "Hormonal Therapy for Prostate Cancer—When to Use it", *Cancer Control*, Jan./Feb. 1995, pp. 32-36.

Thompson, et al., "Loss of p53 Function Leads to Metastasis in ras+myc-Initiated Mouse Prostate Cancer", Abstract for Fogarty International Meeting, Jun. 26-28, 1995.

Xiong, et al. "Human D-Type Cyclin,"*Cell*, vol. 65: pp. 691-699 (May 17, 1991).

Manam, et al., "Dose related changes in the profile of ras mutations in chemically induced CD-1 mouse liver tumors," *Carcinogenesis*, vol. 16(5)pp. 1113-1119 (May 1995).

Blok, et al., "Isolation of cDNA's that are differentially expressed between antrogen-dependent and androgen independent prostate carcinoma cells using differential display PCR."*Prostate*, vol. 26(4), pp. 213-224 (Apr. 1995).

Wu, et al. "Identification of a human hepatocellular carcinoma-associated tumor suppressor gene by differential display polymerase chain reaction," *Life Sciences*, vol. 57(11), pp. 1077-1085 (Nov. 1995).

Schneider, et al. "7,12-Dimethylben[a] anthracene-Induced Mouse Keratinocyte Malignant Transformation Independent of Harvey ras Activation," *J. of Investigative Dermatology*, vol. 101(4), pp. 595-599 (Oct. 1993).

Neumann, H.G., "entstehung und Behandlung von Turoren, Immnunosupressiva", *Allgemeine und Specielle Pharmakologie and Toxikologie*, Edition 5. 1987.

Schlag P.M., "Fruherkennung von Krebs mit Hilfe von molekulariologischen Markem", *Onkologie*, 18, pp. 207, 1995.

Truong, et al. "Association of Transforming Growth Factor-$\beta_1$ with Prostate Cancer: An Immunohistochemical Study," *Human Pathology*, vol. 24, No. 1, pp. 4-9 (Jan. 1993).

Aihara, et al., "Frequency of Apoptotic Bodies Positively Correlates with Gleanson Grade in Prostate Cancer," *Human Pathology*, vol. 25, No. 8, pp. 797-801 (Aug. 1994).

Egawa, et al., "Alterations in mRNA levels for Growth-Related Genes after Transplantation into Castrated Hosts in Oncogene-Induced Clonal Mouse Prostate Carcinoma," *Molecular Carcinogenesis*, vol. 5, pp. 52-61 (1992).

Glenney, "Tyrosine Phosphorylation of a 22-kDa Protein is Correlated with Transformation by Rous Sarcoma Virus," *The Journal of Biological Chemistry*, vol. 264, No. 34, pp. 20163-20166 (1989).

Chen, et al., "Isolation and Characterization of the Promoter Region of Human nm23-H1, a Metastasis Suppressor Gene," Abstract 122:2406 (1994).

Sargiacomo, et al., "Oligomeric Structure of Caveolin: Implications for Caveoale Membrane Organization," *Proc. Natl. Acad. Sci. USA*, vol. 92, pp. 9407-9411 (Sep. 1995).

Tulchinsky, et al., "Transcriptional analysis of the *mts1* gene with specific reference to 5' flanking sequences," *Proc. Natl. Acad. Sci. USA*, vol. 89, pp. 9146-9150 (Oct. 1992).

Yang, et al. "Association of Caveolin Protein with Prostate Cancer Progression", *Journal of Urology*, vol. 157, No. 4, p. 446, Abstract #1742 (Apr. 1997).

Eastham, et al. "Prostate Cancer Gene Therapy: Herpes Simplex Virus Thymidine Kinase Gene Transduction Followed By Ganciclovir in Mouse and Human Prostate Cancer Models", *Human Gene Therapy*, vol. 7, pp. 515-523. Mar. 1, 1996.

Ren, et al. "Identification and characterization of p53 regulated genes in a mouse prostate cancer cell line". AACR Annual Meeting, Mar. 28-Apr. 1, 1998, New Orleans, LA.

Goltsov, et al. "A novel p53-regulated gene encoding a four transmembrane domain protein in mouse prostate cancer cells", AACR Annual Meeting, Apr. 10-14, 1999, Philadelphia, PA.

Ren, et al. "Reduced Lysyl Oxidase in RNA Levels in Experimental and Human Prostate Cancer", *Cancer Research*, vol. 58, pp. 1-6, Mar. 15, 1998.

Nelson, Joel B. "Alternatives to death: Understanding androgen-independent prostate cancer", *Nature Medicine*, vol. 4, No. 9, pp. 1011-1012, Sep. 1998.

Yang et al. "Elevated Expression of Caveolin Is Associated With Prostate and Breast Cancer", *Clinical Cancer Research*, vol. 4, pp. 1873-1880, Aug. 1998.

Fielding, et al. "Caveolin mRNA levels are up-regulated by free cholesterol and down-regulated by oxysterols in fibroblast monolayers", *Proc. Natl. Acad. Sci. USA*, vol. 94, pp. 3753-3758, Apr. 1997.

Nasu, et al. "Suppression of caveoline expression induces androgen sensitivity in metastatic androgen-insensitive mouse prostate cancer cells", *Nature Medicine*, vol. 4, No. 9, pp. 1062-1064, Sep. 1998.

Bist, et al. "Two sterol regulatory element-like sequences mediate up-regulation of caveolin gene transcription in response to low density lipoprotein free cholesterol", *Proc. Natl. Acad. Sci. USA*, vol. 94, pp. 10693-10698, Sep. 1997.

Li, et al. "Src Tyrosine Kinases, G$\alpha$ Subunits, and H-Ras Share a Common Membrane-anchored Scaffolding Protein, Caveolin". *The Journal of Biological Chemistry*, vol. 271, No. 46, pp. 29182-29190, 1996.

Contente, et al., "Expression of Gene *rrg* Is Associated with Reversion of NIH 3T3 Transformed by LTR-c-H-ras", *Science*, vol. 249, pp. 769-798.

Hajnal, et al., "Up-Regulation of Lysyl Oxidase in Spontaneous Revertants of H-ras-transformed Rat Fibroblasts", pp. 4670-4675.

Thompson, et al., "Caveolin-1, a metastasis-related gene that promotes cell survival in prostate cancer", *Apoptosis*, vol. 4, No. 4, pp. 233-237 (1999).

Thompson, et al., "Caveolin-1: a complex and provocative therapeutic target in prostate cancer and potentially other malignancies", *Emerging Therapeutic Targets* 3(2) pp. 337-346 (1999).

Tan, et al., "Identification of the *Lysyl Oxidase* Gene as a Target of the Antioncogenic Transcription Factor, IRF-1, and Its Possible Role in Tumor Suppression", pp. 2417-2421.

Kuivaniemi, et al., "Deficient production of olysyl oxidase in cultures of malignantly transformed human cells", *FEBS Letters*, vol. 195, No. 1, 2, pp. 261-264 (Jan. 1986).

Vater, et al., "Native Cross-Links in Collagen Fibrils Induce Resistance to Human Synovial Collagenase", *Biochem J.*, vol. 181, pp. 639-645 (1979).

Hämäläinen, et al., "Quantitative Polymerase Chain Reaction of Lysyl Oxidase mRNA in Malignantly Transformed Human Cell Lines Demonstrates That Their Low Lysyl Oxidase Activity Is Due to Low Quantities of Its mRNA and Low Levels of Transcription of the Respective Gene", *The Journal of Biological Chemistry*, vol. 270, No. 37, pp. 21590-21593 (Sept. 15, 1995).

Peyrol, et al., "Lysyl Oxidase Gene Expression in the Stromal Reaction to in Situ and Invasive Ductal Breast Carcinoma", *American Journal of Pathology*, vol. 150, No. 2, pp. 497-507 (Feb. 1997).

Thompson, et al., "Exogenous Leukocyte and Endogenous Elastases Can Mediate Mitogenic Activity in Pulmonary Artery Smooth Muscle Cells by Release of Extracellular Matrix-Bound Basic Fibroblast Growth Factor", *Journal of Cellular Physiology*, vol. 166, pp. 495-505 (1996).

Sehgal, et al., "Transforming Growth Factor β1 Stimulates Contrasting Responses in Metastatic versus Primary Mouse Prostate Cancer-derived Cell Lines in Vito", *Cancer Research*, vol. 56, pp. 3359-3365 (Jul. 15, 1996).

Shimura, et al. Abstract; American Urological Association 94th Annual Meeting, Dallas, TX, "Reduction in Lysyl Oxidase Expression is an Preditor of Recurrence Following Radical Prostatectomy", May 1-6, 1999.

Thompson, "Metastasis-related Genes in Prostate Cancer: The Role of Caveolin-1", *Cancer and Metastasis Reviews*, vol. 17, pp. 439-442, 1999.

Guarini, et al., "Transfer of the Interleukin-2 Gene into Human Cancer Cells Induces Specific Antitumor Recognition and Restores the Expression of CD3/T-Cell Receptor Associated Signal Transduction Molecules", *Blood*, vol. 89, No. 1, pp. 212-218 (Jan. 1, 1997).

Jourdan-Le Saux, et al., "Functional Analysis of the Lysyl Oxidase Promoter in Myofibroblast-Like Clones of 3T6 Fibroblast", Journal of Cellular Biochemistry 64: 328-341, Feb. 1997.

*Proceedings of the American Association for Cancer Research*, vol. 36, p. 266 #1589. Mar. 1995.

Liang, Peng, et al., "Differential Display of Eukaryotic Messenger RNA by Means of the Polymerase Chain Reaction", *Science*, vol. 257, pp. 967-971. Aug. 14, 1992.

Wood, David P., Jr., et al., "Sensitivity of Immunohistochemistry and Polymerase Chain Reaction in Detecting Prostate Cancer Cells in Bone Marrow", *The Journal of Histochemistry and Cytochendstry*, vol. 42, No. 4, pp. 505-511. 1994.

Gudas, "Retinoids, Retinoid-responsive Genes, Cell Differentiation, and Cancer", *Cell Growth & Differentiation*, vol. 3, pp. 655-662, Sep. 1992.

Mokulis, et al., "Screening for Prostate Cancer: Pros, Cons, and Reality", *Cancer Control*, pp. 15-21, Jan./Feb. 1995.

Parton, Robert G., "Ultrastructural Localization of Gangiosides; GM 1 is concentrated in Caveolae", *The Journal of Histochemistry and Cytochemistry*, vol. 42, No. 2, pp. 155-166.

Wu, M., et al., "Clustering of GPI-Anchored Folate Receptor Independent of Both Cross-Linking and Associatoin wit Caveolin", *The Journal of Membrane Biology*, 159, pp. 137-147.

Garver, William S., et al., "Increased Expression of Caveolin-1 in Heterozygous Niemann—Pick Type II Human Fibroblasts", *Biochemical and Biophysical Research Communications*, 236, pp. 189-193.

Parton, Robert G., "Caveolin-3 Associates with Developing T-tubules during Muscle Differentiation", *The Journal of Cell Biology*, vol. 136, No. 1, Jan. 13, 1997, pp. 137-154.

Feron, Oliver, et al., "Endothelial Nitric Oxide Synthase Targeting to Caveolae", *The Journal of Biological Chemistry*, vol. 271, No. 37, pp. 22810-22814.

Moore, Robert H., et al., "Ligand—stimulated B2-adrenergic Receptor Internalization via the Constitutive Endocytic Pathway into rab5-containing Endosomes", *Journal of Cell Science*, 108, pp. 2983-2991.

Scherer, Philipp E., et al., "Caveolin Isoforms Differ in Their N-terminal Protein Sequence and Subcellular Distribution", *The Journal of Biological Chemistry*, vol. 270, No. 27, pp. 16395-16401.

Brown, Dennis, et al., "Antigen Retrievl in Cryostat Tissue Sections and Cultured Cells By Treatment with Sodium Dodecyl Sulfate (SDS)", *Histochem Cell Biol*, (1996), 105, pp. 261-267.

Song, Kenneth S., et al., "Expression of Caveolin-3 in Skeletal, Cardiac, and Smooth Muscle Cells", *The Journal of Biological Chemistry*, vol. 271, No. 25, pp. 15160-15165.

Eastham, et al. "In Vivo Gene Therapy with p53 or p12 Adenovirus for Prostate Cancer", *Cancer Research*, vol. 55, p. 5151-5155, Nov. 15, 1995.

Eastham, et al. "Transforming Growth Factor-$\beta_1$: Comparative Immunohistochemical Localization in Human Primary and Metastatic Prostate Cancer",*Laboratory Investigation*, vol. 73, No. 5, pp. 628-635 (1995).

Aihara, et al. "The Frequency of Apoptosis Correlates with the Prognosis of Gleason Grade 3 Adenocarcinoma of the Prostate". *Cancer*, vol. 75, No. 2, pp. 522-529 (Jan. 15, 1995).

Yang, et al., "Perineural Invasion of Prostate Carcinoma Cells is Associated with Reduced Apoptotic Index", *Cancer*, vol. 78, No. 6, pp. 1267-1271 (Sept. 15, 1996).

Chamness, et al., "The effect of androgen on nitric oxide synthase in the male reproductive tract of the rat", *Fertility and Sterility*, vol. 63, No. 5, pp. 1101-1107 (May 1995).

Stapleton, et al., "Primary Human Prostate Cancer Cells Harboring p53 Mutation are Clonally Expanded in Metastates", *Clinical Cancer Research*, vol. 3, pp. 1389-1397 (Aug. 1997).

Koleske, et al., "Reduction of caveolin and caveolae in oncogenically transformed cells",*Proc. Natl. Acad. Sci. USA*, vol. 92, pp. 1381-1385 (Feb. 1995).

Kagan, Herbert M., "Regulation of Matrix Accumulation", Academic Press, Inc., pp. 321-398 (1986).

Kagan, et al., "Properties and Function of Lysyl Oxidase", *AM. J. Respir. Cell Mol. Biol.*, vol. 5, pp. 206-210 (1991).

Aihara, et al., "Frequency of Apoptotic Bodies Positively Correlates with Gleason Grade in Prostate Cancer", Human Pathology, vol. 25, No. 8, pp. 797-801 (Aug. 1994).

Feres-Filho, et al., "Pre- and Post-translational Regulation of Lysyl Oxidase by Transforming Growth Factor-β1 in Osteoblastic MC3T3-E1 Cells", *The Journal of Biological Chemistry*, vol. 270, No. 51, pp. 30797-30803 (Dec. 22, 1995).

Shanley, et al., "Transforming growth factor-$\beta_1$ increases lysyl oxidase enzyme activity and mRNA in rat aortic smooth muscle cells", *Journal of Vascular Surgery*, vol. 25, No. 3, pp. 446-452 (Mar. 1997).

Boak, et al., "Regulation of Lysyl Oxidase Expression in Lung Fibroblasts by Transforming Growth Factor-$\beta_1$ and Prostaglandin $E_2$", *American Journal of Respiratory Cell and Molecular Biology*, vol. 11, pp. 751-755 (1994).

Kavirikko, et al., "Posttranslational Modifications of Collagen and Their Alterations in Heritable Diseases", pp. 263-292.

Danks, David M., "Disorders of Copper Transport: Menkes Disease and the Occipital Horn Syndrome", *Connective Tissue and Its Heritable Disorders*, pp. 487-505 (1993).

Kivirikko, Kari L., "Collagens and their Abnormalities in a Wide Spectrum of Diseases", *Annals of Medicine 25*: pp. 113-126 (1993).

* cited by examiner

METHODS FOR THE TREATMENT OF NEOPLASTIC DISORDERS WITH ANTI-CAVEOLIN AGENTS

This application is a continuation of application U.S. Ser. No. 10/151,055, filed May 21, 2002 now abandoned, which is a continuation of application U.S. Ser. No. 09/797,969, filed Mar. 5, 2001 now U.S. Pat. No. 7,029,859, which is a continuation of U.S. Ser. No. 09/186,184, filed Nov. 5, 1998, now U.S. Pat. No. 6,252,058, which claims priority of U.S. Provisional Application Ser. No. 60/064,351, filed Nov. 5, 1997.

RIGHTS IN THE INVENTION

This invention was made in part with United States Government support under grant number CA350129, awarded by the National Cancer Institute, National Institute of Health. The United States Government has certain rights in the invention.

BACKGROUND

1. Field of the Invention

The present invention relates to methods for the identification and use of metastatic sequences, such as the caveolin gene, to target metastatic cells. The invention further relates to the use of diagnostic and therapeutic agents based on these metastatic sequences for the treatment of neoplastic disorders.

2. Description of the Background

The development of higher organisms is characterized by an exquisite pattern of temporal and spatially regulated cell division. Disruptions in the normal physiology of cell division are almost invariably detrimental. One such type of disruption is cancer, a disease that can arise from a series of genetic events.

Cancer cells are defined by two heritable properties, uncontrolled growth and uncontrolled invasion of normal tissue. A cancerous cell can divide in defiance of the normal growth constraints in a cell leading to a localized growth or tumor. In addition, some cancer cells also gain the ability to migrate away from their initial site and invade other healthy tissues in a patient. It is the combination of these two features that make a cancer cell especially dangerous.

An isolated abnormal cell population that grows uncontrollably will give rise to a tumor or neoplasm. As long as the neoplasm remains noninvasively in a single location, it is said to be benign, and a complete cure may be expected by removing the mass surgically. A tumor or neoplasm is counted as a cancer if it is malignant, that is, if its cells have the ability to invade surrounding tissue. True malignancy begins when the cells cross the basal lamina and begin to invade the underlying connective tissue. Malignancy also occurs when the cells gain the ability to detach from the main tumor mass, enter the bloodstream or lymphatic vessels, and form secondary tumors or metastases at other sites in the body. The more widely a tumor metastasizes, the harder it is to eradicate and treat.

As determined from the epidemiological and clinical studies, most cancers develop in slow stages from mildly benign into malignant neoplasms. Malignant cancer usually begins as a benign localized cell population with abnormal growth characteristics called dysplasia. The abnormal cells acquire abnormal growth characteristics resulting in a neoplasia characterized as a cell population of localized growth and swelling. If untreated, the neoplasia in situ may progress into a malignant neoplasia. Several years, or tens of years may elapse from the first sign of dysplasia to the onset of full blown malignant cancer. This characteristic process is observed in a number of cancers. Prostate cancer provides one of the more clear examples of the progression of normal tissue to benign neoplasm to malignant neoplasm.

The walnut-sized prostate is an encapsulated organ of the mammalian male urogenital system. Located at the base of the bladder, the prostate is partitioned into zones referred to as the central, peripheral and transitional zones, all of which surround the urethra. Histologically, the prostate is a highly microvascularized gland comprising fairly large, glandular spaces lined with epithelium which, along with the seminal vesicles, supply the majority of fluid to the male ejaculate. As an endocrine-dependent organ, the prostate responds to both the major male hormone, testosterone, and the major female hormones, estrogen and progesterone. Testicular androgen is considered important for prostate growth and development because, in both humans and other animals, castration leads to prostate atrophy and, in most cases, an absence of any incidence of prostatic carcinoma.

The major neoplastic disorders of the prostate are benign enlargement of the prostate, also called benign prostatic hyperplasia (BPH), and prostatic carcinoma, a type of neoplasia. BPH is very common in men over the age of 50. It is characterized by the presence of a number of large distinct nodules in the periurethral area of the prostate. Although benign and not malignant, these nodules can produce obstruction of the urethra causing nocturia, hesitancy to void, and difficulty in starting and stopping a urine stream upon voiding the bladder. Left untreated, a percentage of these prostate hyperplasias and neoplasias may develop into malignant prostatic carcinoma.

In its more aggressive form, malignant transformed prostatic tissues escape from the prostate capsule and metastasize invading locally and throughout the bloodstream and lymphatic system. Metastasis, defined as tumor implants which are discontinuous with the primary tumor, can occur through direct seeding, lymphatic spread and hematogenous spread. All three routes have been found to occur with prostatic carcinoma. Local invasion typically involves the seminal vesicles, the base of the urinary bladder, and the urethra. Direct seeding occurs when a malignant neoplasm penetrates a natural open field such as the peritoneal, pleural or pericardial cavities. Cells seed along the surfaces of various organs and tissues within the cavity or can simply fill the cavity spaces. Hematogenous spread is typical of sarcomas and carcinomas. Hematogenous spread of prostatic carcinoma occurs primarily to the bones, but can include massive visceral invasion as well. It has been estimated that about 60% of newly diagnosed prostate cancer patients will have metastases at the time of initial diagnosis.

Prostate cancer is the most common malignancy in men in the USA, resulting in an estimated 41,800 deaths in 1997. (Parker S L, et al., *CA Cancer J Clin* 47: 5-27, 1997). The widespread use of prostate-specific antigen (PSA) has dramatically increased the number of patients diagnosed with prostate cancer and generally lowered the stage of disease at diagnosis. (Scardino P T, *Urol. Clin. N. Am.* 16:635-655, 1989; Epstein J L, et al., *JAMA* 271: 368-374, 1994). Nevertheless, 5%-10% of cancers detected by PSA screening are clinically advanced and not candidates for radical prostatectomy. Despite surgical removal of the prostate, 30%-60% of men treated will have recurrence of cancer within 5 years, suggesting that the clinical stage of the patients undergoing surgery was highly inaccurate. 20%-57% of patients undergoing definitive surgery with presumed localized disease will have rising PSA following treatment, also indicative of local or distant residual disease. (Ohori M, et al., *J. Urol.* 154: 1818-1824, 1995; Zeitman A L, et al., *Urology* 43: 828-833, 1994). Unfortunately, neither of these conditions is amenable to curative therapy.

Surgery or radiotherapy is the treatment of choice for early prostatic neoplasia. Surgery involves complete removal of the entire prostate (radical prostatectomy), and often removal of the surrounding lymph nodes, or lymphadenectomy. Radiotherapy, occasionally used as adjuvant therapy, may be either external or interstitial using $^{125}$I. Endocrine therapy is the treatment of choice for more advanced forms. The aim of this therapy is to deprive the prostate cells, and presumably the transformed prostate cells as well, of testosterone. This is accomplished by orchiectomy (castration) or administration of estrogens or synthetic hormones which are agonists of luteinizing hormone-releasing hormone. These cellular messengers directly inhibit testicular and organ synthesis and suppress luteinizing hormone secretion which in turn leads to reduced testosterone secretion by the testes. In normal prostate, removal of androgenic hormones results in regression of the gland involving apoptosis of more than 60% of the luminal epithelial cells. Although often initially sensitive to removal of androgens, prostate cancer cells eventually lose this response and continue to grow and spread even in the absence of androgenic steroids. Despite the advances made in achieving a pharmacologic orchiectomy, the survival rates for those with late stage carcinomas are rather bleak.

Current therapeutic regimens for metastatic disease typically involve both chemical and surgical androgen ablation, which although has been demonstrated to extend life when compared to untreated patients, almost invariably results in the development of hormone-refractory disease and the demise of the patient. The fundamental concepts upon which current androgen ablation therapy was developed were reported more than 50 years ago by Huggins and Hodges. (Huggins C, et al., *Cancer Res.* 1:293-297, 1941). These experiments reported the phenomenon in which removal of androgenic steroids by castration resulted in reduced growth and biochemical activities in prostate cancer.

With the advent of molecular biology, various investigators in laboratories have attempted to understand the molecular biology of castration-induced regression of the prostate at a more mechanistic level. The model systems selected almost invariably compared mRNAs produced prior to castration and during castration-induced regression using rat prostate model systems in vivo. These model systems yield gene activities that may be involved in castration-induced regression but could also be involved in activities that are not directly relevant or related to castration-induced regression but were stimulated by removal of androgenic steroids. It is anticipated that only a small fraction of gene activities modulated by steroid withdrawal would indeed be involved in castration-induced regression and, therefore, significant confounding background activity would be seen in these existing model systems. There is therefore a need for a model system in which the nonrelevant androgenic-stimulated gene activities would be normalized. Moreover, a better understanding of the molecular basis of metastasis as well as hormone insensitivity would allow rational efforts toward the development of novel effective anti-metastasic therapy to proceed.

SUMMARY OF THE INVENTION

The present invention overcomes the problems and disadvantages associated with current strategies and designs and provides new methods for the use of sequences related to metastasis, such as the caveolin gene, for the evaluation, diagnosis and treatment of neoplastic disorders such as, for example, prostate cancer.

Surprisingly, caveolin expression increases in metastatic human prostate cancer cells as compared to primary prostate tumors. According to the methods of the present invention, certain cancers may be treated by suppressing expression of the caveolin gene in metastatic cells or cells predisposed to metastasis. As caveolin expression correlates with metastasis, application of biological technologies designed to block the activity of caveolin or the function of caveolae may be used for the treatment of neoplastic disorders, including human prostate tumors.

Accordingly, one embodiment of the invention is directed to a method for treating a patient having a metastatic tumor by delivering a therapeutically effective amount of an antisense caveolin nucleic acid to the patient. The nucleic acid may comprise, for example, RNA, DNA or PNA, and be expressed using any suitable means, such as a viral vector. Useful viral vectors include vaccinia virus vectors, retrovirus vectors, adenovirus vectors and combinations thereof. The antisense sequence may encode the entirety of or, alternately, an effective portion of the caveolin-1 gene, such as the scaffolding domain or the dimerization domain. Alternately, the effective portion may comprise the transcription promoter of the caveolin-1 gene. In the latter embodiment, the promoter may be functionally coupled to a gene which encodes an anti-metastatic therapeutic agent.

Another embodiment of the invention is directed to a method for treating a metastatic disorder, such as metastatic prostate or breast cancer, by administering to a patient having the disorder an effective amount of an anti-caveolin antibody. The antibody may be reactive against all or an effective portion of caveolin, such as the scaffolding domain or the dimerization domain of a caveolin protein.

Still another embodiment is directed to a method for evaluating the metastatic potential of a primary prostate tumor by contacting a sample of the tumor with an anti-caveolin antibody coupled to a detectable marker and then determining the amount of antibody bound to the sample. The anti-caveolin antibody may be a monoclonal or polyclonal antibody, and may be optionally coupled to a detectable label.

Still another embodiment of the invention is directed to a method for treating a patient for prostate cancer by suppressing caveolin expression by the prostate cancer and reducing the level of androgen in the patient. Caveolin expression may be suppressed by administering an anti-sense caveolin nucleic acid to the patient. Androgen levels may-be reduced by any suitable means, such as by administering anti-androgen therapy to the patient.

Still another embodiment is directed to an isolated promoter, such as a caveolin promoter, that is specific for expression in metastatic cells. The promoter may further comprise a gene which encodes an anti-metastatic therapeutic agent. The. therapeutic agent may be a toxin, apoptotic inducer, cytokine, such as IL-2, or other suitable agent.

Other objects and advantages of the invention are set forth in part in the description which follows, and in part, will be obvious from this description, or may be learned from the practice of the invention.

DESCRIPTION OF THE INVENTION

Figure 1:
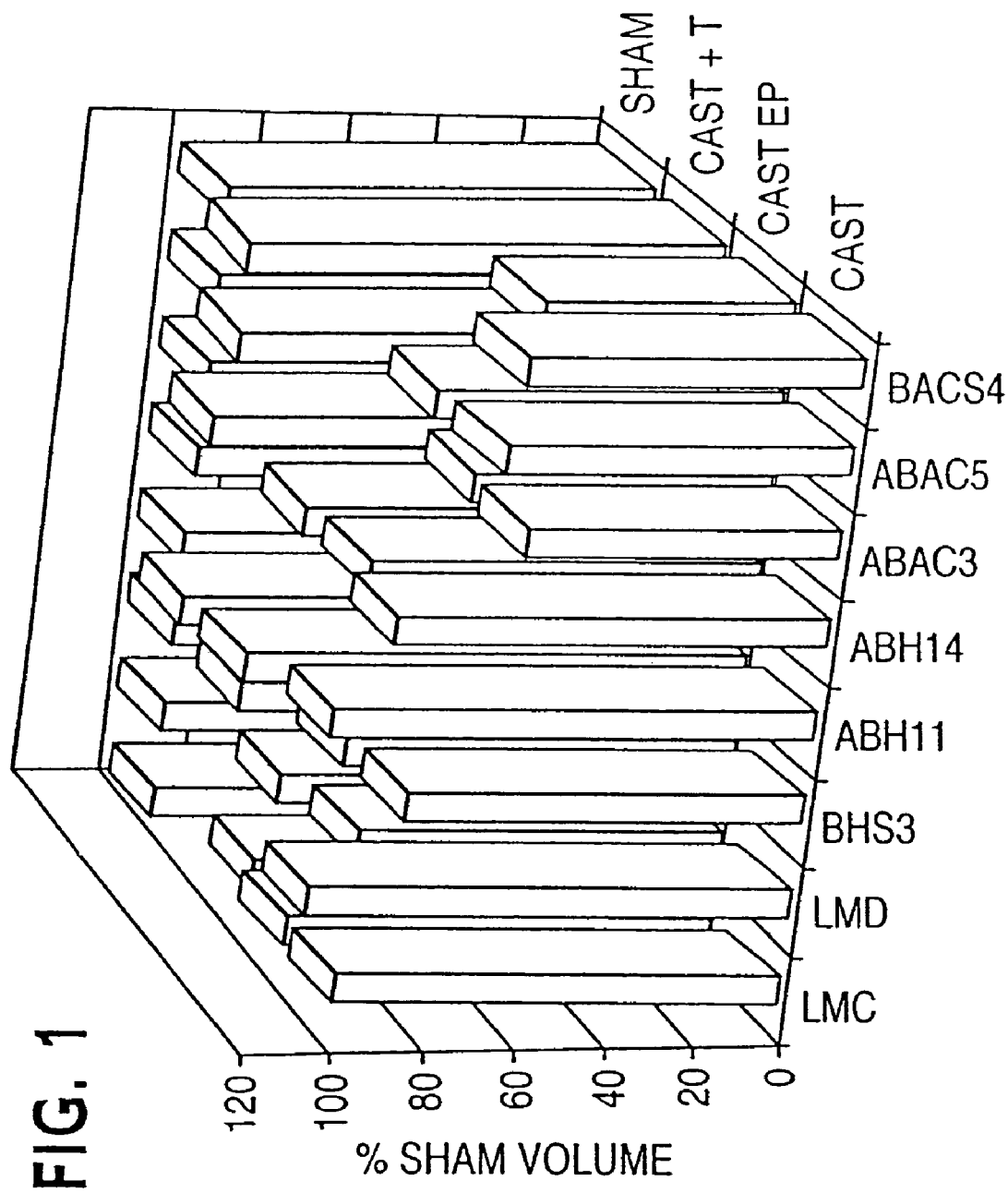
FIG. 1 Graphic depicting restoration of androgen sensitivity by antisense caveolin in three independent cell lines.

As embodied and broadly described herein, the present invention is directed to methods for the detection, diagnosis and treatment of disorders related to metastasis, and to diagnostic kits which comprise metastatic sequences.

The ability of cancers to metastasize makes tumors difficult to eradicate by any means. Malignant cancer involves a multistage progression from, for example, normal tissue through hyperplasia, early adenoma, early carcinoma and finally to a metastatic tumor. Cells of a typical tumor loosen their adhesion to their original cellular neighbors and cross the basal lamina and endothelial lining to enter the body's circulation. Once in circulation, the metastatic cell exits from the circulation to disseminate throughout the body-and proliferate in a new environment.

Like the initial oncogenic event, the ability of a cell to metastasize requires additional mutationic or epigenetic changes. An understanding of the molecular mechanisms of metastasis allows for the design of treatments to inhibit metastasis. Knowledge of stage specific gene expression for neoplastic disorders allows for early detection and typing of tumors. With early detection and typing, proper treatment may be administered to a patient with the neoplastic disorder earlier, which will lead to a higher probability of a complete cure.

For human prostate tumors, the study of stage specific tumors is difficult, if not impossible, as cell lines are extremely difficult to grow and it is rare that tissue becomes available from the primary tumor as well as metastatic disease from the same patient. This problem is exacerbated because of the infrequent biopsy of metastatic deposits in concordance of isolation of material from the primary tumor. Furthermore, the growth of cell lines from malignant prostates has proved to be problematic over the last few decades. This is evidenced by the lack of cell lines from prostate cancer obtained under any conditions.

One embodiment of the invention is directed to a method for identifying a metastatic sequence. A mammalian cell is transformed into a pre-neoplastic or neoplastic state or phenotype by transfection with one or more oncogenic sequences. Alternatively, or in addition to transfection, the mammalian cell may be treated with an agent or subjected to a condition that potentiates the metastatic character of the cell or predisposes the cell to metastasis. The transfected or treated cell is implanted into a host animal at a primary site and grown for a period of time sufficient to develop a metastasis at a secondary site. Expressed sequences from cells of the primary site and cells at the secondary site are amplified by differential display polymerase chain reactions. PCR products from these reactions are compared and the metastatic sequence identified by alteration in the levels or patterns of the resulting products.

Mammalian cells from a wide variety of tissue types and species are suitable for transfection or treatment including surgically obtained or primary or immortalized cells and cell lines. Cells may be from humans or primates, mice, rats, sheep, cows, rabbits, horses, pigs or guinea pigs or from transgenic or xenogeneic host mammals. Cells may be obtained from adult, juvenile or fetal tissue, and used directly from the mammal, from cryogenically preserved samples, or after culturing in vitro or in vivo for a period of time. In vitro culturing typically involves tissue culture conditions (e.g. 37° C.; 5% $CO_2$) while in vivo culturing may involve successive passage of cells through host animals such as, for example, mice or rabbits. Cells passed in vivo may be obtained from sites proximal or distal to the site of implantation. The tissue type from which the cells are derived or obtained may be any tissue which is susceptible to transfection or other treatment including, for example, urogenital tissues, epithelial cells, hepatic cells, fibroblasts lymphatic tissues, hematopoietic cells, cells of the immune system, cells of the gastrointestinal system and cells of the nervous system.

Cell types useful for the identification of metastatic sequences related to prostate cancer include cells and cell lines of the fetal prostate lineage from normal or transgenic animals, and cells from normal or reconstituted prostate tissue. One method of generating reconstituted prostate cells is to isolate fetal prostate tissue and micro dissect the fetal prostate epithelium away from fetal mesenchyme. Fetal prostate epithelium may be genetically manipulated before reassociation with fetal mesenchyme. Genetic manipulation involves treatment or transfection with a metastatic agent or a nucleic acid sequence that affects neoplastic or metastatic potential of the cell. Reassociation of fetal epithelium and mesenchyme is performed by implanting epithelial tissue within a pocket of mesenchymal tissue. After manipulation, cells are reimplanted into a mammalian host in a similar manner as other cells, such as reimplantation into or under the renal capsule.

Mammalian cells may be transfected by a variety of techniques, all of which are well-known to those of ordinary skill. Direct methods involve the introduction of genetic material into the nucleus of a cell by injection. These techniques include high velocity projectile injection, microinjection, and electroporation. Indirect methods involve the active or passive uptake of the genetic information by the cell. Indirect techniques include transduction with recombinant vectors, and chemical or physical treatments such as calcium phosphate uptake, lipofection or dextran sulfate transfection. Chemical techniques rely on chemical carriers to introduce nucleic acids into a cell. These methods, for example, utilize unilamellar phospholipid vesicles (e.g. liposomes) loaded with DNA (or RNA). The approach relies on the fusion of the DNA containing vesicles with the plasma membrane of the recipient cells. After entry, DNA traverses the cytoplasm and enters the nucleus. Another lipofection technique uses a synthetic cationic lipid such as N-[1-(2,3-dioleyloxy)propyl]-N, N,N-trimethylammonium chloride (DOTMA). DOTMA spontaneously associates with nucleic acids and forms unilamellar vesicles upon sonication. Genetic material is incorporated into these vesicles and subsequently transfected into the cell. Calcium phosphate co-precipitation involves mixing of purified nucleic acid with buffers containing phosphate and calcium chloride which results in the formation of a fine precipitate. Presentation of this precipitate to cells results in incorporation of the nucleic acid into cellular genome. Other chemicals, such as DEAE dextran or polybrene, when present in media with nucleic acids, can also cause the transfection of mammalian cells.

Physical methods of transfection rely on electric fields, needles and particles to enable nucleic acids to traverse the cellular membrane. Electric field mediated DNA transfection, commonly called electroporation, is based on the principle that membranes, when subjected to an electric field, undergo a reversible breakdown resulting in pores large enough to permit the passage of nucleic acids. In microprojectile mediated gene transfer, micro-projectiles of subcellular dimensions are coated with nucleic acid and propelled at high velocity into a cell using a particle gun. The nucleic acid is introduced into the nucleus directly when the particles impinge upon the nucleus. In microinjection, nucleic acid is injected directly into the nucleus of a cell with a needle. Lasers have also been used to introduce minute holes in cellular membranes to allow introduction of nucleic acids. All-these methods may be used for transfection and the selection of the method will depend on the cell type, the desired transfection efficiency and the equipment available.

The efficiency of transfection may be monitored and enhanced by the co-transfection of a selectable marker. If a marker is co-transfected with a genetic construct, positively transformed cells may be separated from nontransformed cells by chemical selection. The efficiency of transfection will be increased in most cases because the chemicals will selectively kill non-transfected cells. The number of transfected cells may also be monitored by analyzing the degree of chemical resistance of the transfected cells. Markers commonly used for selection purposes include, for example, nucleic acids encoding dihydrofolate reductase, metallothionein, CAD, adenosine deaminase, adenylate deaminase, UMP synthetase, IMP 5'-dehydrogenase, xanthine-guanine phosphoribosyltransferase, mutant thymidine kinase, mutant HGPRTase, thymidylate synthetase, P-glycoprotein 170, ribonucleotide reductase, glutamine synthetase, asparagine synthetase, arginosuccinate synthetase, ornithine decarboxylase, HMG-CoA reductase, N-acetylglucosaminyl transferase, theronyl-tRNA synthetase, sodium or potassium dependent ATPase or derivatives or mutants of these nucleic acids. Markers may be used individually or in combination. Chemicals useful for selection include methotrexate, cadmium, PALA, Xyl-A, adenosine, 2'-deoxycoformycin, adenine, azaserine, coformycin, 6-azauridine, pyrazofuran, mycophenolic acid, limiting xanthine, hypoxanthine, aminopterin, thymidine, 5-fluorodeoxyuridine, adriamycin, vincristine, colchicine, actinomycin D, puromycin, cytocholasin B, emetine, maytansine, Bakers' antifolate, aphidicolin, methionine sulfoximine, β-aspartyl hydroxamate, albizziin, canavanine, α-difluoromethylomithine, compactin, tunicamycin, borrelidin, ouabain, and derivatives and analogs and combinations of these chemicals. Some chemicals, such as methotrexate, may be used individually while other chemicals, such as HAT (hypoxanthine, aminopterin and thymidine), need to be used in combination to be effective.

The oncogene transfection efficiency, the fraction of live cells transfected by an oncogene, may be indirectly enhanced by chemical selection for a co-transfected marker. An oncogene is a sequence which can predispose, or induce the cell into a pre-neoplastic or neoplastic condition or otherwise enhance the metastatic potential of the cell. Sequences with these properties are referred to as oncogenes and include abl, ahi, akt, bcl, crk, dsi, erb, ets, evi, fes/fps, fim, fis, fgr, flv, fms, fos, gin, gli, int, jun, kit, mas, lck, met, mil/raf, mis, mlv, mos, myb, myc, neu, onc, pim, raf, ras, rel, ros, seq, sis, ski, spi, src, tcl, thy, trk, and yes. Some oncogenes, such as ras, are oncogenic when mutated. Other oncogenes, such as myc, are oncogenic when overexpressed or underexpressed. Many oncogenes represent members of multigene families or homolog families. Homologs are proteins that have similar primary, secondary or tertiary structures. Genes may differ in nucleic acid sequence or encoded peptide sequence and still be homologs when the encoded polypeptides have similar spatial folding. Many oncogenes can be classified into dominant oncogenes and recessive oncogenes. One or more dominant oncogenes can confer a neoplastic or pre-neoplastic phenotype to a cell. One or more recessive oncogenes, when silenced, may also confer a neoplastic or preneoplastic phenotype. Gene silencing is performed by transfecting cells with nucleic acids which cause genetic ablation or by antisense suppression.

While any oncogene may be used, the preferred oncogenes are those that are normally associated with metastasis such as a metastasis specific gene. Such genes include for example, TGF-β1, Cyclin D1 p21, p34, p53, lysyl oxidase, caveolin, actin binding protein, ubiquitin activating enzyme E1, nmb or α-actinin 3. Metastatis-specific genes may be used individually or in combination with other oncogenes.

The metastatic potential of a cell may be altered, for example, by gene ablation with a sequence specific for a recessive oncogene. Recessive oncogenes are those genes which encode products which can suppress oncogenesis and metastasis. A gene ablation sequence can be designed to specifically suppress a recessive oncogene. Ablation may include pre-transcriptional inhibition such as homologous recombination with endogenous recessive oncogenes and post transcriptional inhibition such as the expression of antisense oncogenes to suppress translation. Gene ablation sequences may be targeted towards well known recessive oncogenes such as, for example, the retinoblastoma gene (Rb) or Bcg. Other candidates for ablation include metastatic genes previously isolated by the invention such as, for example, TGF-β1, cyclin D1, p21, p34, p53, lysyl oxidase, caveolin, actin binding protein, ubiquitin activating enzyme E1, nmb or α-actinin-3. The effects of ablating a recessive oncogene may include oncogenesis and metastases.

Alternatively, or in addition to transfecting the mammalian cell may be treated with an agent, either before or after transfection, that alters the expression of the cell's nucleic acids. Treatment may comprise contacting the cells with one or more agents which affect the neoplastic character (e.g. neoplastic agents; phorbol esters), metabolization (e.g. metabolic agents), metastatic character (e.g. metastatic agents), differentiation (e.g. differentiation agents; retinoic acid), activation or proliferation (e.g. growth factors) of the cell. Agents which can alter gene expression include chemicals such as benzanthracene (BA), dimethyl benzanthracene (DMBA) or 5-azacytidine. Alternatively, treatment may also comprise altered conditions such as hypoxia which involves subjecting a cell to a reduced oxygen content, exposable to radiation or other stresses to the cell.

Treatment may be in vitro or in vivo and may include for example, direct or indirect induction or suppression of well known oncogenic sequences and genes isolated by the invention such as, for example, TGF-β1, Cyclin D1, p53, lysyl oxidase, caveolin, actin binding protein, ubiquitin activating enzyme E1, nmb, α actinin 3, and p34. Gene expression induction includes transfecting expression vectors encompassing coding regions of the gene. Gene repression comprises introducing a gene ablation sequence or a repressor of the gene to the cell.

Cells which have one or more genes ablated may also be used. For example, a metastatic suppressor gene may be ablated to prevent inhibition to metastases. A useful gene for ablation is a gene capable of affecting the phenotype and behavior of a cell or tumor. For example, with prostate tumors, suitable genes include both well known genes and genes isolated by the methods of the invention such as for example, TGF-β1, Cyclin D1, p21, p34, p53, lysyl oxidase, caveolin, actin binding protein, ubiquitin activating enzyme E1, nmb and α actinin 3. Genetic ablation (gene knockout) refers to a process of silencing the expression of a particular gene in a cell. The silencing process may include, for example, gene targeting or antisense blocking. Gene targeting refers to a process of introducing a nucleic acid construct into a cell to specifically recombine with a target gene. The nucleic acid construct inactivates the targeted gene. Inactivation may be by introduction of termination codons into a coding region or introduction of a repression site into a regulatory sequence. Antisense blocking refers to the incorporation into a cell of expression sequences which directs the synthesis of antisense RNA to block expression of a target gene. Antisense RNA hybridizes to the mRNA of the target gene to inhibit expression.

The host animal is preferably the same species as the implanted cell. In cases of xenogeneic transplants, the host may be immunocompromised genetically or by treatment with drugs such as immunosuppressants. A host may be immunocompromised genetically by breeding such as with nude mice or severe combined immunodeficient (SCID) mice. A host may also be immunocompromised by chemical or irradiation methods. An additional route to immunocompromise a host is to use transgenic technology to introduce an immunosuppressing gene or to introduce a foreign antigen gene. An immunosuppressing gene is a gene that affects the efficiency of the immune system such as a gene which inhibits the formation of cells of the B cell or T cell lineage. A foreign antigen gene, when expressed, may cause the host to tolerate the antigens in a xenogeneic transplant and not mount an immune response.

Cells may be implanted into any primary site in a host animal, such as, for example, subcutaneous implantation, intravenous injection, or implantation into the abdominal cardiac, chest, pulmonary, thoracic or peritoneal cavity. Using techniques known to those of ordinary skill in the art, cells can be placed on or in nearly any organ or tissue. Reasons for choosing a site include ease of implant, proximity of similar tissue type, immunoprivileged position and ease of inspection. Metastases migrate from the primary site to one or more secondary sites such as, for example, the lung, kidney, liver, lymph nodes, brain, testis, bone, spleen, ovaries or mammary tissue. Preferred sites include the renal capsule, the testes, the prostate and the ovaries.

To avoid histocompatibility problems, the implant may be placed into a histocompatible host animal. Such problems are generally avoided if the host animal is syngeneic. Alternatively, a non-histocompatible host may be used if the host can be made immunotolerant. Hosts may also be transgenic or immunocompromised animals or genetically matched to the mammalian cells to be introduced. Immunocompromised animals may be derived from established mouse lines such as nude mice or severe combined immune deficiency (SCID) mice, or by treatments such as radiation, chemical, pharmaceutical or genetic targeting. Sufficiently immunosuppressed animals can be made tolerant to xenogeneic transplants.

After implantation the host animal is maintained under normal conditions to develop metastases. Alternatively, the host animal may be subjected to an altered treatment or environmental condition to stimulate or repress metastasis or induce other cellular functions. In metastasis, a sub-population of cells of the implantation site invade and establish one or more secondary colonies in the host animal. The behavior of the implanted cell will depend on the cell type, the transfected sequence and the implantation location. Typical secondary sites for metastatic colonies include lung, kidney, liver, lymph nodes, brain, testis, spleen, bone, ovary, skin and mammary tissue. Metastatic development times vary from days to weeks even months. Cells with a high metastatic potential tend to progress to metastasis quickly while cells with a low metastatic potential may require very long periods of time that span significant portions of the life span of the animal.

The host animal may be analyzed for metastatic development weekly, from one week to 20 weeks to six months, nine months or one year after implantation. For animals with longer life spans such as sheep, the animal may be inspected yearly from one year on up to ten years for metastatic tumors. Metastases can be detected by examinations such as palpation, biopsy, imaging, exploratory surgery, CAT scans, autopsy, X-ray and direct observation. In addition, tissue samples may be taken surgically from the host mammal and subjected to histological or other examination for the detection of metastases.

Expressed sequences include mRNA, rRNA, hnRNA, DNA, cDNA and any nucleic acid sequence that is expressed in the cell. These sequences may be amplified by in situ techniques or by purification of nucleic acid from collected cells. Expressed sequences may be obtained by extracting nucleic acids from cells before implantation, at the primary site or at the secondary site. Cells collected at these sites may optionally be cultured for a time before nucleic acid extraction. The effects of treatment with gene expression modifying agents or environmental conditions can be ascertained by collecting cells before and after treatment. Treatment may be applied to the cells while the cells are in the host mammal or after the cells are excised and in culture. Nucleic acids are collected from cells using techniques that are well known to those of ordinary skill in the art.

Expressed sequences may be used directly for polymerase chain reaction (PCR) analysis using, for example, the technique of reverse transcriptase polymerase chain reaction (RT-PCR). Alternatively, RNA may be enriched for mRNA using a poly-A RNA enrichment method. Numerous poly-A RNA enrichment methods exist and are commercially available. Techniques used for poly-A RNA enrichment include oligo-dT columns, oligo-dT magnetic beads, and oligo-dT cellulose. RNA may be further processed into cDNA before analysis by reverse transcription using reverse transcriptase. The cells or the extracted nucleic acid may be preserved, such as by freezing, and analyzed at a later time.

Differential display polymerase chain reactions (DD-PCR) are performed on the expressed sequences using two variable primers which may contain the same or entirely different sequences or an anchor primer and a variable primer. If an anchor primer is used, one anchor primer and one variable primer create a single or a single set of reaction products for each reaction. A complete profile may include 25 or more different PCR reactions per sample wherein each PCR reaction is performed with the same anchor primer and a different variable primer. DD-PCR may also be performed using anchor and variable primers which contain the same sequence. Whether a particular reaction is used depends on whether a difference exists between the products of two PCR reactions using the same primers. When a significant difference exists between the expression sequences amplified, one pair of PCR reactions may be sufficient and informative.

Anchor primers are preferably oligonucleotides with a poly-T sequence at the 5'-terminals and a dinucleotide selected from the group consisting of AA, AG, AC, AT, GA, GG, GC, GT, CA, CG, CC and CT at the 3'-terminals. For example, the sequence may be 5'-TTTTTTAA-3' or 5'-TTTTTTAG-3'. The length of the poly-T sequence is typically between about 5 to about 30 bases in length and preferably between about 10 to about 20 nucleotides long. The total length of the anchor primer can vary greatly for each experiment but is preferably between about 7 to about 32 and more preferably between about 12 and about 22. Differential diagnostic polymerase chain reaction may also be performed using an anchor primer of any sequence and a length between about 5 to about 30, preferably between about 5 to about 20 and more preferably between about 7 to about 12 bases.

The variable primer may comprise a random sequence, or a specific sequence. Variable primers preferably are oligonucleotides with a length between about 5 to about 30, preferably between about 5 to about 20, and more preferably between about 7 to about 12 bases in length.

To enhance detection of the PCR product, the anchor primer or the variable primer, or both, may comprise a detectable moiety. Examples of detectable moieties include radioactive moieties, phosphorescent moieties, magnetic moieties, luminescent moieties, conjugatable moieties or other detectable moiety. A plurality of detectable moieties may be used to enhance detection or to simplify data analysis. Other detectable moieties include conjugatable moieties and molecules which can bind specifically to other molecules which are themselves detectable. Examples of conjugatable moieties include avidin, streptavidin, biotin, antibody, antigen, cell adhesion molecules and other molecules with similar activities. Detectable moieties are preferably labeled nucleotides. A nucleotide may be any natural or synthetic nucleotide or nucleotide analog capable of incorporation into an elongation reaction in a polymerase chain reaction. Labeled nucleotides include nucleotide triphosphates labeled with one or more radioactive atoms such as $^{32}P$, $^{33}P$, $^{3}H$, $^{14}C$ and $^{35}S$.

Products of DD-PCR reactions are compared to detect the metastatic sequence. Comparisons can be performed between expressed sequences from cells at secondary sites with cells at any stage in the method including untreated mammalian cells, transfected or treated mammalian cells, implanted-cells or cells obtained from the primary site in the host animal. DD-PCR products may be analyzed by any method which reliably compares the products of two polymerase chain reactions. Typical analytical methods used for this purpose include polyacrylamide gel electrophoresis, capillary electrophoresis and high pressure liquid chromatography (HPLC). Product produced from DD-PCR may be analyzed in double-stranded or single-stranded forms. When the products of the DD-PCR reaction are labeled the sizes and distribution of the products may be monitored and analyzed by following the labels using a radiation monitor or by autoradiography. For example, DD-PCR performed in the presence of radioactive primers or nucleotide triphosphates, can be analyzed by gel electrophoresis, by capillary electrophoresis, or by HPLC. Products are easily monitored by the presence of radioactivity.

Another method for analyzing and isolating metastatic sequences is to sequence the amplified nucleic acid sequences. Sequencing may be performed using standard methods well known to those of ordinary skill in the art. The resulting sequence may be compared to a sequence database created or well-known, such as Genbank, for identification or for locating homologs. The sequencing information may be used to calculate the physical characteristics of the nucleic acids such as melting temperature and secondary structure. The primary sequence and the physical characteristic may be used to synthesize optimal nucleic acid probes for the detection or staging of metastasis or conditions that are predictive of the presence or absence of the metastatic condition.

Another embodiment of the invention is directed to a method for identifying a metastatic sequence. A mammalian cell is pretreated with a metastatic agent to form a population of cells predisposed to metastasize. The treated cells are introduced into a host mammal at a primary site. The host animal is maintained for a period of time sufficient to develop a metastasis at a secondary site. Expressed sequences of cells at the primary site and cells at the secondary site are treated with a genotoxic agent or subjected to genotoxic conditions. Expressed sequences of the treated cells are amplified by differential display polymerase chain reaction and compared with untreated cells from any previous step to identify the metastasis sequence.

The metastatic agent may be a chemical compound, a nucleic acid or a protein that alters the metastatic potential of a cell or relates to or is associated with the metastatic process. Chemical compounds include retinoids such as 4-hydroxyphenyl (4HP). Other agents include the proteins TGF-β1, Cyclin D1, p21, p34, p53, lysyl oxidase, caveolin, actin binding protein, ubiquitin activating enzyme E1, nmb or α-actinin 3, or their respective genes. The metastatic agent may be a metastatic stimulant or a metastatic suppressant. Metastatic stimulants may be used to enhance the sensitivity of the metastasis sequence detection method. Conversely metastatic suppressants may be used to decrease the sensitivity of the method enabling the selective identification of potent metastatic sequences or sequences specific to a particular tissue type or metastatic disorder. Treatment may comprise direct contact with the metastatic agent or incubation for a period of time. Metastatic agents enhance the metastatic potential of the implanted cells and increase the sensitivity and the speed of the overall method.

The cells at the primary site and the metastatic cells at the secondary site may be treated with a genotoxic agent in vivo or in vitro. In vivo treatment may comprise injecting genotoxic agents directly into the host mammal or specifically applying the agent with, for example, topical formulations. The cells at the primary site and the secondary site may also be isolated from the host animal and treated with the genotoxic agent in culture. Genotoxic agents are chemical compounds, nucleic acids or proteins that alter gene expression by affecting the nucleic acid genome directly by, for example, chemical modification, or indirectly by, for example, altering components associated with gene expression. Such agents include, for example, benzanthracene (BA), dimethyl benzanthracene (DMBA) and 5-azacytidine, and may include metastatic agents as well. In addition to or in place of genotoxic agents, the cells may be treated to hypoxic conditions or radiation to alter gene expression. Metastatic sequences identified in these methods may be specific for particular genotoxic agents or conditions.

Another embodiment of the invention is directed to the use of a host animal with an altered genotypic or phenotypic predisposition for metastases. A host animal may be screened for endogenous expression of a metastasis gene. Particularly useful metastatic sequences include TGF-β. A host animal with reduced levels of a metastatic gene product may be used to isolate novel metastatic genes. Host animals may be screened for reduced levels of metastatic gene expression. In addition, transgenic technology may be used to ablate a metastatic gene in the germline of a host animal.

Another embodiment of the invention is directed to analysis of a cell line before their use as a starting material to isolate metastatic genes in a particular pathway. Analysis is useful in identifying cells, and consequently sequences specific to these cells, which are particularly susceptible or resistant to metastatic transformation. For example, a cell highly predisposed to metastasis may be especially sensitive for detecting metastatic genes. Conversely, a cell showing high resistance to metastasis can be used to isolate especially potent metastatic sequences. One method to analyze susceptibility to metastasis is to determine the cellular response to growth factors or growth inhibitors. Briefly, a control population and a test population of cells are exposed to a growth factor or a growth inhibitor and the cellular response (e.g. proliferation, metabolism) recorded. Cells showing abnormal responses to the growth factor or growth inhibitor may be used as the starting material for metastatic gene isolation. Cellular responses include changes in the rate of cellular division (e.g. thymidine uptake), changes in the expression of RNA or proteins, changes in cellular localization or modification patterns of RNA or proteins, and changes in the rate of uptake, release or metabolism of nutrients.

Especially potent or weak metastatic genes may be detected by treating and analyzing the metastatic potential of different cells and selecting a suitable cell type as the starting material. For example, cells may be treated with myc, ras, p53 or combinations thereof and analyzed for cyclin D1 expression which is shown to correlate with metastasis. The gene expression pattern of cyclin D1 in MPR correlates with that of human prostate tumors analyzed with stains specific for cyclin D1 expression. Normal human tissue shows no cyclin D1 expression or staining. Moderately differentiated prostate cancers with dispersed or focal positively staining show moderate staining. Advanced poorly differentiated prostate cancer shows strong nuclear as well as cytoplasmic staining implying strong expression of cyclin D1. After treatment with myc, ras or p53, cyclin D1 expression shows correlation with the metastatic potential of the cell. Thus, cyclin D1 expressing cells are a source of cells with high metastatic potential. Conversely, cells with low cyclin D1 expression are a source of potentially metastatically resistant cells.

This method may be adjusted for the isolation of metastatic sequences expressed along a particular developmental or differentiation pathway by combining the various treatment and analytical techniques. For example, a mammalian cell may be genetically ablated for TGF-β1, Cyclin D1, p53, lysyl oxidase, caveolin, actin binding protein, ubiquitin activating enzyme E1, nmb, α actinin 3, or p34. The genetically altered cell is used in an in vivo mouse prostate reconstitution (MPR) model. Metastatic and nonmetastatic cells isolated from the MPR may be analyzed directly or after induction with an agent such as the TGF-β gene or its product. Analysis involves the use of differential display polymerase chain reaction to identify differentially expressed bands. Sequences identified may be used for subsequent ablation, transformation or differential analysis.

Genetic ablation (gene knockout) may be performed after a cell is selected or by selecting a cell comprising a genotype with the proper genetic ablation. Cells already comprising gene ablation may be acquired from a cell depository, from other laboratories or from a transgenic animal. As transgenic animals comprise genetically ablated genes in every cell, any tissue from a transgenic animal may be used as the starting material.

The effects of oncogenes are at least additive and often synergistic. Thus, dominant oncogenes may be transfected together or multiple recessive oncogenes ablated together for a stronger effect. Furthermore, both methods may be combined and dominant oncogene transfection may be accompanied by recessive oncogene ablation.

The function of the metastatic sequence may be determined by the differential expression pattern. For example, a dominant metastatic gene will be present in a metastatic cell while a recessive metastatic gene will be present in a non-metastatic cell. Metastatic sequences may be detected as bands which are present in the DD-PCR of metastases isolated in secondary sites and absent from DD-PCR products of primary cells. These sequences may be dominant metastatic genes whose expression is directly responsible for metastases, or they may be metastasis associated genes whose expression correlates with metastasis. Either are useful for therapy and diagnosis. Conversely, DD-PCR bands which are present in primary site tumors, but absent in secondary metastatic sites, may be dominant metastasis suppression genes. Dominant metastasis suppression genes comprise genes whose expression suppresses metastasis while nonmetastatic genes comprise genes whose expression correlates with nonmetastatic tissue. Genes which are highly correlative with either the metastatic phenotype or the non-metastatic phenotype may be isolated. Isolation can be performed by cutting the appropriate nucleic acid in the band of a polyacrylamide gel or by collecting the appropriate fraction in an HPLC or capillary electrophoresis. The nucleic acid may be cloned into a plasmid vector, and sequenced, or synthetically prepared.

Another embodiment of the invention is directed to a method for identifying sequences in a metastatic pathway which are responsive or unresponsive to extracellular signals. Such sequences may be used in therapy and diagnosis of metastatic disorders. Implanted cells or cells from a primary site and cells from a secondary site are treated with extracellular signals. RNA sequences from the treated cells are compared with RNA sequences of the untreated cells. Treated cells and untreated cells may be derived from a short term or long term in vitro culture of primary tumor and malignant tumors. Alternatively, a part of a primary tumor and a part of a malignant tumor may be collected before the animal is treated with an extracellular cytokine or other factor. Long term cultures, or cell lines of primary and malignant cells may also be used as recipients of extracellular growth signal treatment. Suitable signals for each experiment will depend on the cell type. Generally, growth factors, lymphokines, inhibitory factors, migratory factors or hormones may be used. Factors previously isolated by commercial or methods of the invention and factors associated with or causative or suppressive of metastasis are preferred. Thus, transforming growth factor β1 (TFG-β1) may be used to treat cells before DD-PCR analysis. Proteins encoded by the genes isolated by this method are especially useful for the treatment of cells for the isolation of additional sequences. The identification of one sequence responsive to the extracellular signal pathway allows for identification of additional genes upstream and downstream from that sequence.

Another embodiment of the invention is directed to metastatic sequences identified by the methods of the invention. Metastatic sequences are sequences associated with the presence or absence of a metastasis or related to the metastatic processor can be used in the therapeutic treatment of metastasis. Metastatic-related sequences include dominant metastatic sequences, recessive metastatic sequences, metastasis associated sequences, dominant oncogenes, recessive oncogenes and cell cycle genes. These genes encode for example, proteins involved in cell cycle, signal processing, DNA replication, growth regulation, inter and intra cellular signaling transcription control and translation control. Isolated sequences are useful in the treatment and for the detection of metastatic and other disorders. Disorders which may be treated comprise diseases involving proteins and sequences which are isolated by interaction with the sequences and proteins isolated by the method of the invention. Both malignant or nonmalignant disorders may be treated. Non malignant disorders include hyperplasia, dysplasia and hypertrophy. Examples of nonmalignant disorders include benign enlargement of the prostate, nodular hyperplasia, and benign prostatic hypertrophy.

Treatment may involve gene replacement, gene targeting, antisense inhibition, gene expression or gene suppression. Gene replacement involves replacing a copy of a defective gene with another copy by homologous recombination. Gene targeting involves the disruption of a cellular copy of a gene by homologous recombination. Antisense inhibition exploits the specificity of hybridization reactions between two complementary nucleic acid chains to suppress gene expression. Cloned genes can be engineered to express RNA from only one or the other DNA strands. The resultant RNA hybridizes to the sense RNA and inhibits gene expression. Gene expression and gene suppression involve the introduction of genes whose expression actively inhibits neoplastic transformation and metastasis.

Another embodiment of the invention is directed to nucleic acids which comprise a sequence identified by the methods of the invention. The nucleic acid may be DNA, RNA or PNA and may be used as a diagnostic tool in the treatment of neoplastic disorders and malignant tumors. The nucleic acids may comprise additional sequences such as promoters, for expression of a sense or antisense message, recombination sequences for gene targeting, selectable markers for transfections, or replication origins for passage in a prokaryotic or eukaryotic host such as animal cells, bacteria or yeast.

Another embodiment of the invention is directed to nucleic acids which comprise sequences identified by the method of the invention such as, for example, the caveolin, ABP280 (actin binding protein 280), the lysyl oxidase gene, and the nmb gene (clone 29). Nucleic acids comprising a sequence corresponding to these genes may be used in treatment or diagnosis and in diagnostic kits for screening biological samples for the presence or absence of metastasis or metastatic potential. Treatment may involve using the sequences in gene therapy, including gene ablation, gene expression and antisense suppression. Diagnosis may involve genotypic analysis of samples to determine the existence and expression levels of the expressed sequences.

Another embodiment of the invention is directed to methods for treating a neoplastic disorder comprising administering a pharmaceutically effective amount of composition containing a nucleic acid having a sequence identified according to the methods of this invention, its expression product or fragments of either. The nucleic acid may be in the form of a sense or antisense single-stranded or double-stranded nucleic acid. The composition may be combined with a pharmaceutically acceptable carrier such as water, alcohols, salts, oils, fatty acids, saccharides, polysaccharides administered by injection, pulmonary absorption, topical application or delayed release. More than one carrier may be used together to create a pharmaceutical with desirable properties.

Another embodiment of the invention is directed to a kit or diagnostic aid for screening biological samples for detection of metastasis or neoplasia. The kits comprising sequences isolated according to the methods of the invention and reagents and materials useful in such kits, such as, for example, buffers, salts, preservatives, and carriers, all of which are well known to those of ordinary skill in the art. Kits are useful for the analysis of tissues to screen those for the determination of normal, nonmalignant, neoplastic or malignant cells. Kits may comprise additional reagents useful for the extraction of nucleic acids from a tissue sample. Reagents for analyzing the nucleic acid extracted from a tissue sample such as polymerase chain reaction reagents and Southern blot reagents may also be included.

Another embodiment of the invention is directed to the use of the caveolin gene and protein in the isolation of oncogenes and in the treatment of neoplastic disorders such as, for example, prostate cancer. Caveolin is an integral membrane protein and a principal component of caveolae. Caveolae are small invaginations at or near the plasma membrane of most smooth muscle cells and may function as a component of specific signal transduction pathways. Surprisingly, caveolin expression increases in metastatic human prostate cells as compared to human primary prostate tumors.

As caveolin expression correlates with metastasis, application of biological technologies designed to block the activity of caveolin or the function of caveolae may have therapeutic benefits for the treatment of neoplastic disorders such as human prostate tumors. Specific treatment approaches using caveolin may include the delivery of antisense or dominant negative caveolin sequences using expression or viral vectors, as well as the use of specific anti-caveolin antibodies. Additional approaches could also target the caveolae, but are not specifically based on caveolin function. Additional protein and non-protein components of caveolae could also be targeted for abrogation or the local or systemic administration of a nutritional or biological agent may also be used. For example, caveolae are extremely rich in cholesterol and disruption or depletion of this molecule may alter the function of caveolae.

Multiple genetic activities are involved in androgen ablation-induced prostate regression, yet very little is known regarding the rate limiting steps in the molecular cascade that leads to regression, or the molecular basis of hormone resistance in prostate cancer. A mouse model has been developed to identify metastasis-related genes in prostate cancer. This model includes a series of clonal cell lines derived from prostate cancer metastases that developed in vivo using the mouse prostate reconstitution (MPR) model system.

One of the gene products found to be associated with metastasis in this mouse model as well as in human prostate cancer is caveolin. The subsequent production of stably selected clones with antisense caveolin resulted in a significant reduction in metastatic activities relative to vector-control clones and parent cell lines. Surprisingly, it has been discovered that tumors produced by the antisense caveolin clones significantly regressed in response to surgical castration in vivo. Eleven days following androgen ablation, tumors derived from three independent antisense clones regressed by approximately 30% relative to the wet weights-produced in either vector-control clones or parental clones which did not respond to castration therapy under the same conditions. The antisense caveolin tumors that responded to castration therapy also demonstrated significantly increased levels of apoptosis relative to either vector-control clones or parental cell lines. Therefore, the data indicates that reduction of caveolin levels not only suppresses metastatic activity but also restores androgen sensitivity. These results are believed to establish a new paradigm for understanding androgen refractory disease and open the door for new innovations in prostate cancer therapy.

Specifically, panels of clonal cell lines were derived from primary prostate tumors as well as metastases from the same animal using an MPR mouse model system for prostate cancer metastasis. Within this panel of cell lines, there are sets that are both genetically and biologically matched such that the primary genetic difference between these cell lines should be related to metastatic activities. This is made possible, in part, by unique retroviral integration sites that serve as markers for clonality. Using a modified differential display-polymerase chain reaction (DD-PCR) approach, numerous genes were identified that are related to metastasis in human prostate cancer. For example, the caveolin gene was found to be up-regulated in metastasis-derived cells relative to their primary tumor-derived counterparts. (Yang, G. et al., Clin. Can. R. 4:1873-1880, 1998). The caveolin gene was first identified as the major phospho-protein in src transformed cells (Glenney J R, *J. Biol. Chem.* 264:20163-20166, 1989) and was shown to be the major structural component of caveolae. (Lisanti M P, et al., *Mol. Memb. Biol.* 12:121-124, 1995). Caveolae are membrane domains which may compartmentalize some single transduction pathways, and recent identification of an integrin/urokinase plasminogen activator receptor (uPAR)/caveolin complex (Wei Y, et al., *Science* 273: 1551-1555, 1996) provides a mechanistic framework for linking alterations of caveolin expression with two potentially important properties of malignant progression of metastasis-integrin mediated cell-cell adhesion and uPAR mediated proteolytic activity. With commercially available antiserum to caveolin, increased protein levels in both mouse and human prostate metastases have been confirmed. (Yang, G. et al., Clin. Can. R. 4:1873-1880, 1998). Further, the expression of caveolin in three mouse metastatic cell lines has been experimentally suppressed by expression of an antisense cDNA construct. Suppression of caveolin does not reduce the growth potential of mouse prostate cancer cells, but does reduce both the incidence of metastatic spread and the actual tumor volume of lymph node metastases. (Yang, G. et al., Clin. Can. R. 4:1873-1880, 1998).

Surprisingly, it has been discovered that the antisense caveolin clones have also acquired hormone sensitivity. Orthotopic tumors that form from antisense caveolin clones, but not vector-control clones or parental cells, regress by approximately 30% in wet weight following surgical castration. Further studies confirm increased levels of apoptosis in antisense caveolin tumors relative to non-regressing control tumors. Continuous massaging of three antisense caveolin tumors in castrated male hosts resulted in increased caveolin protein levels. This data indicates that caveolin alone is responsible, in part, for the development of hormone-refractory prostate cancer in the present model system. These novel results should have a significant impact on prostate cancer by: 1) spawning additional investigations that will reveal the molecular pathway leading from the androgen ablation stimulus to regression of prostate cancer in vivo; 2) leading to a more complete understanding of the molecular basis of hormone-refractory prostate cancer; and 3) ultimately leading to the development of anti-metastasis therapy based on small molecule, immunological or gene therapy approaches. Future studies will likely result in tremendous therapeutic impact on men in that suppression of caveolin or other molecules in the caveolin-androgen resistance pathway will lead to effective anti-metastasis therapy.

As noted, an animal model has been developed for experimental prostate cancer research, the mouse prostate reconstitution (MPR) model. (Thompson, T C, et al., *Cell* 56:917-930, 1989). A unique and significant feature of this "transgenic gland" model is that by manipulating the number and types of initiating genetic events, it can be used to produce and study every step of carcinogenesis, from premalignant changes through the metastatic cascade. (Thompson T C, et al., *Mol. Carcinog.* 7:165-179, 1993; Thompson T C, et al., *Oncogene* 10:869-879, 1995). Experiments using the MPR model have also provided numerous cell lines that have been utilized extensively for both in vitro and in vivo studies. Significant advances in understanding prostate cancer metastasis have come from analyzing cell lines that were derived from either a primary tumor or a tumor at a metastatic site.

Since the tumor was initiated by retrovirus infection, primary tumor- and metastasis-derived cells from the same animals that are clonally related may be compared, based on unique retrovirus integration sites. Differential display PCR has been adapted and refined to compare mRNA from clonally matched cell lines and identify numerous genes that appear to be metastasis specific.

One of the first of such genes identified was the gene for caveolin, a major structural component of an organelle termed caveolae. It has subsequently been confirmed in animal models and in human prostate and breast cancer that increased levels of the caveolin protein are associated with metastasis (Yang, G. et al., Clin. Can. R. 4:1873-1880, 1998). This provides another example validating the importance of the selected animal model since many discoveries made using this model have also been found to be relevant to human prostate cancer. (Truong L D, et al., *Hum. Pathol.* 24:4-9, 1993; Thompson T C, et al., *J. Cell. Biochem.* 16(S):54-61, 1992; Eastham J A, et al., *Lab Invest.* 73:628-635, 1995; Williams R H, et al., *Clin. Cancer Res.* 2:635-640, 1996; Eastham J, et al., *Clin. Cancer Res.* 1:1111-1118, 1995; Yang G, et al., *Clin. Cancer Res.* 2:635-640, 1996; Stapleton A M F, et al., *Clin. Cancer Res.* 3:1389-1397, 1997; Aihara M, et al., *Hum. Pathol.* 25:797-801, 1994; Aihara M, et al., *Cancer* 75:522-529, 1995; Yang G, et al., *Cancer* 78:1267-1271, 1996).

Surprisingly, it has been discovered that when tumor-bearing animals are castrated following orthotopic injection of metastatic cell lines with antisense caveolin (ABAC3, ABAC5, and BACS4) tumor volume is reduced relative to sham surgery-treated animals or castrated animals that received a testosterone implant. For example, as shown in FIG. 1, antisense caveolin has been shown to restore androgen sensitivity in 3 independent cell lines. As depicted in FIG. 1, orthotopic tumors were initiated by injecting 5000 cells into the dorsal prostate of 129 male mice. Three days later the animals were castrated (cast) or sham operated. Some animals also received implants of silastic tubing containing testosterone proprionate (cast+T) or an empty pellet (cast EP). Tumor volume was determined after 2 weeks. All values for ABAC3, ABAC5, and BACS4 in the cast and cast EP groups are significantly different from cast+T pellet and sham controls ($p<0.05$).

In contrast to the antisense tumors, two parental cell lines (148-1LMD and 151-2LMC) as well as control vector only clones (ABH11, ABH14 and BHS3) did not respond to androgen withdrawal. Significantly increased apoptosis is believed responsible, in part, for the regression, and that in addition to growth suppression, a reduction in metastasis also occurs following castration only in the antisense clones.

The model system has been generated based on the finding that high caveolin levels block castration-induced prostatic regression, and reduction in caveolin levels appear to release this block. This model is believed to normalize the nonrelevant androgenic-stimulated gene activities. This model system involves clonal cell lines in which caveolin levels have been selectively reduced by stable antisense caveolin transfection as well as the production of clonal vector control cell lines. When these cell lines are injected orthotopically in vivo, allowed to produce tumors (that are of equivalent size at 3 days post inoculation), and subjected to hormone manipulation, only the antisense caveolin stable clones undergo castration-induced regression, whereas the vector control clones and their parental cells do not. Therefore, in this model system, the gene activities that are not directly involved with castration-induced regression, but are induced or repressed following the castration stimulus, should be present in both vector control clones as well as antisense caveolin clones. The only differences in the gene activities between the two groups of cell clones in response to the castration stimulus should be related to castration-induced regression which occurs only in the antisense caveolin clones.

Transgenic mouse model systems have thus far proved to be invaluable tools for understanding gene functions within a complex biological milieu in vivo. Over the past 10 years hundreds if not thousands of transgenic mice have been generated and used to unravel the phenotypic effects of tissue-specific gene expression within the context of normal gene activities, i.e., normal mouse development in vivo. A transgenic mouse with targeted expression of caveolin to the prostate gland would produce significant and important information regarding the impact of overexpression of caveolin on normal mouse prostatic development as well as the possible pathological consequences of this gene activity.

During normal development, the mouse prostate undergoes extensive growth and morphogenesis in response to androgenic steroids. (Cunha G R, et al., *J. Androl* 13:465475, 1992). Preliminary data indicates that overexpression of caveolin can block castration-induced regression of mouse prostate cancer. Therefore, it seems likely that overexpression of caveolin would block the normal testosterone-stimulated growth and development of mouse prostate. The growth and development that occurs in prostatic tissue in the mouse is not only dependent on increasing testosterone concentrations that occur with reproductive maturity but also fluctuations in testosterone that occur shortly after birth. (Cunha G R, et al., *J. Androl* 13:465-475, 1992). It is believed that under the influence of caveolin overexpression, a normal mouse prostate would be insensitive to such changes and an aberrant phenotype would be produced.

The present invention is directed to effective therapies for prostate cancer metastasis through increased understanding of the molecular mechanisms. Preliminary data indicates that overexpression of caveolin blocks the castration-induced pathway that leads to apoptosis-mediated regression of mouse prostate cancer in vivo. One possible explanation is that the caveolin protein is binding inducible nitric oxide synthase and inhibiting activity following an initial castration-induced stimulus. (Chamness S L, et al., *Fertil. Steril.* 63:1101-1107, 1995). Therefore, reduction of caveolin levels in human prostate cancer prior to androgen ablation therapy would likely convert it from androgen-insensitive to androgen-sensitive and result in increased tumor regression. The present invention relates to methods for producing significant reductions in caveolin protein prior to androgen ablation therapy. The molecular tools for applying anti-caveolin therapy include recombinant adenoviral vector systems, antisense oligonucleotides, retroviral vector systems, and small molecule and antibody interference.

The production of a transgenic mouse that overexpresses caveolin under the transcriptional control of the MMTV or the probasin promoter will result in overgrowth and abnormal differentiation of the mouse prostate in vivo. During development, the mouse prostate is exquisitely sensitive to changes in circulating androgen levels. Aberrant expression of caveolin will block the response to androgenic stimuli to a great extent, and prostatic epithelium in male caveolin-transgene mice will be deregulated for growth and differentiation.

Significantly reducing caveolin levels using specific gene-based technologies will result in reacquisition of sensitivity to castration in hormone-refractory mouse and, hopefully, human prostate cancer. Recombinant adenoviral vectors may be used to over express antisense caveolin directly in mouse prostate cancer. Following treatment with antisense caveolin adenovirus, subsequent castration therapy will result in enhanced sensitivity of prostatic tumors to the stimulus and, therefore, more widespread apoptosis in cancer cells. This therapy will have application to human disease.

The present invention relates to methods to determine the molecular pathways of castration-induced regression in mouse prostate cancer vis-á-vis the caveolin overexpression model system by, inter alia, assessment of specific apoptotic activities and gene activities previously shown to accompany castration-induced regression in both rodent and human model systems. In addition, differential display (DD)-PCR may be used to identify specific gene activities that are directly related to castration-induced regression using the unique model system of the present invention and ultimately, specific signal transduction pathways may be tested.

The present invention also relates to the generation of transgenic mice in which overexpression of caveolin expression is targeted to the prostate gland. Analyses of these mice can be used to determine the extent of developmental abnormalities and pathological changes that occur. Hormone manipulation of these mice can provide insights into prostatic growth, morphogenesis and therapeutic efficacy in vivo.

The present invention also relates to the potentiation of androgen ablation therapy by reduction of caveolin protein using adenoviral vector systems, antisense oligonucleotides, antisense retroviral vectors, and small molecules and antibodies. Optimal methodologies may be selected for the coupling of these therapies with surgical castration in an attempt to produce more widespread cell death in mouse prostate cancer.

Some of the potential therapeutic and diagnostic applications of the present invention include:

1. Antisense Applications:

An antisense caveolin RNA strand may be used for a number of applications, including antisense blocking or antisense inhibition. Antisense blocking refers to the incorporation into a cell of expression sequences which direct the synthesis of antisense RNA to block expression of a target gene. Antisense RNA hybridizes to the mRNA of the target gene to inhibit expression.

Antisense inhibition also exploits the specificity of hybridization-reactions between two complementary nucleic acid chains to suppress gene expression. If a cloned gene is engineered so that only the opposite DNA strand is transcribed, the resultant RNA may hybridize to the sense RNA and inhibit gene expression.

2. Domain-specific Applications:

There are three genes in the caveolin family, caveolin-1, caveolin-2 and caveolin-3. Two domains have been identified on caveolin-1 that have important biological functions. One mediates dimerization between caveolin-1 and caveolin-2. This dimerized caveolin spontaneously leads to the formation of caveolae.

The other domain is called the scaffolding domain. It mediates the binding of some, but certainly not all, of the specific proteins that can initiate signal transduction. These sites on caveolin can serve as potential targets for drugs or peptides that interfere with or modify these biological activities. For example, these sequence sites could be the subject of gene targeting or other diagnostic and therapeutic strategies.

3. Interference Peptides:

In addition, small interference peptides may be chemically linked to steroids to allow for both specificity of cell target as well as the specificity of intercellular pathway.

4. Viral Vectors and Non-viral Approaches:

Specific treatment approaches using caveolin may include the delivery of antisense or dominant negative caveolin sequences using expression or viral vectors or non-viral approaches.

5. Caveolin Gene Promoter Approaches:

The caveolin gene promoter, which has been cloned, can be used for cell targeting of anti-caveolin molecules or other therapeutic genes.

The high caveolin prostate cancer cells, and possibly high caveolin breast cancer cells, are the cells that are more likely to metastasize, because they can survive in the vasculature and lymphatics where concentrations of growth factors and testosterone are very low compared to the prostate per se. In addition, the normal blood vessel endothelium expresses high levels of caveolin; thus, the killing of these cells would promote overall tumor death. This makes the caveolin promoter an advantageous target over others.

6. Use of Caveolin as Biomarker:

Caveolin is up-regulated by cholesterol, insulin-like growth factor 1 and testosterone. As these factors may be risk-factors for the development and/or progression of prostate and breast cancer, caveolin may serve as an intermediate biomarker for the adverse effects of these dietary/hormonal elements.

Caveolin levels in African-American prostate cancer are four times higher than that in Caucasian prostate cancer, which has been controlled for stage and grade of cancer. African-Americans have a much higher rate of progression and mortality from prostate cancer than Caucasians.

The caveolin promoter (in the mouse gene only so far) has an unusual region of di-nucleotide and tri-nucleotide repeats that could be highly mutable. This may explain the "genetic difference" in caveolin expression in African Americans versus Caucasians in response to, perhaps, dietary cholesterol.

The following experiments are offered to illustrate embodiments of the invention and should not be viewed as limiting the scope of the invention.

EXAMPLES

Example 1

Caveolin Immunoassay in Human Prostate Cancers

Primary site human prostate tumors and metastases were isolated and analyzed for caveolin expression by immunoassay. The results of the assay are shown in Table 1. Metastases show higher levels of caveolin proteins in metastases than in primary tumors. Immunohistology of tissue sections reveals both elevated levels and distinct distribution of caveolin protein in metastatic human prostate when compared to a primary human prostate tumor.

TABLE 1

| Patients | Primary-site | Metastases in lymph node |
|---|---|---|
| 1 | + | ++ |
| 2 | ++ | +++ |
| 3 | ++ | +++ |
| 4 | ++ | ++ |
| 5 | + | + |
| 6 | ++ | ++ |
| 7 | ++ | +++ |
| 8 | + | + |
| 9 | − | − |
| 10 | + | + |
| 11 | + | + |
| 12 | ++ | ++ |
| 13 | + | + |
| 14 | ++ | +++ |

Example 2

Correlation of Caveolin Expression and Androgen Sensitivity

In this example, molecular pathways of castration-induced regression in mouse prostate cancer vis-á-vis the caveolin overexpression model are determined. Specific apoptotic activities and gene activities previously shown to accompany castration-induced regression in both rodent and human model systems are assessed. Differential display (DD)-PCR is used to identify specific gene activities that are directly related to castration-induced regression using the unique model system of the present invention, and specific signal transduction pathways are evaluated.

Levels of caveolin expression may be correlated with androgen sensitivity. This phenomenon is also reversible. Correlation experiments are performed using a single androgen-sensitive caveolin antisense clone (ABAC3) and re-selecting for the androgen-insensitive phenotype by passing this cell line as an orthotopic tumor through a series of castrated male host animals. Three sequential passages of 14 days each are undertaken, following inoculation of 5,000 cells into the dorsolateral prostate, according to our standard methods. (Hall S J et al., Clin. Exp. Metastasis 15: 484-493, 1997).

After each 14-day growth period the tumor is weighed and tissue is frozen for future analysis of gene activities and protein levels. A portion of the tumor is fixed in formalin for imnmunohistochemistry. Following the third 14-day growth period in castrated hosts, in vitro cell outgrowths from monocellular dispersions are derived from the tumors, and both a derived cell line as well as a single cell suspension of the tumor are tested for hormone sensitivity by injecting 5,000 cells into a normal male host animal, allowing 3 days' growth and then subjecting the host animal to various hormone treatments that include sham surgery; surgical castration; surgical castration plus testosterone propionate (TP) pellet; and surgical castration plus empty pellet. This evaluates whether androgen sensitive tumors have been selected.

The tissues are subsequently analyzed for caveolin using immunohistochemistry as well as Western blotting, and are analyzed for AR levels using a monoclonal antibody recently obtained from Michael McPhaul, Texas Southwestern University, Dallas, Tex.

Figure 2:
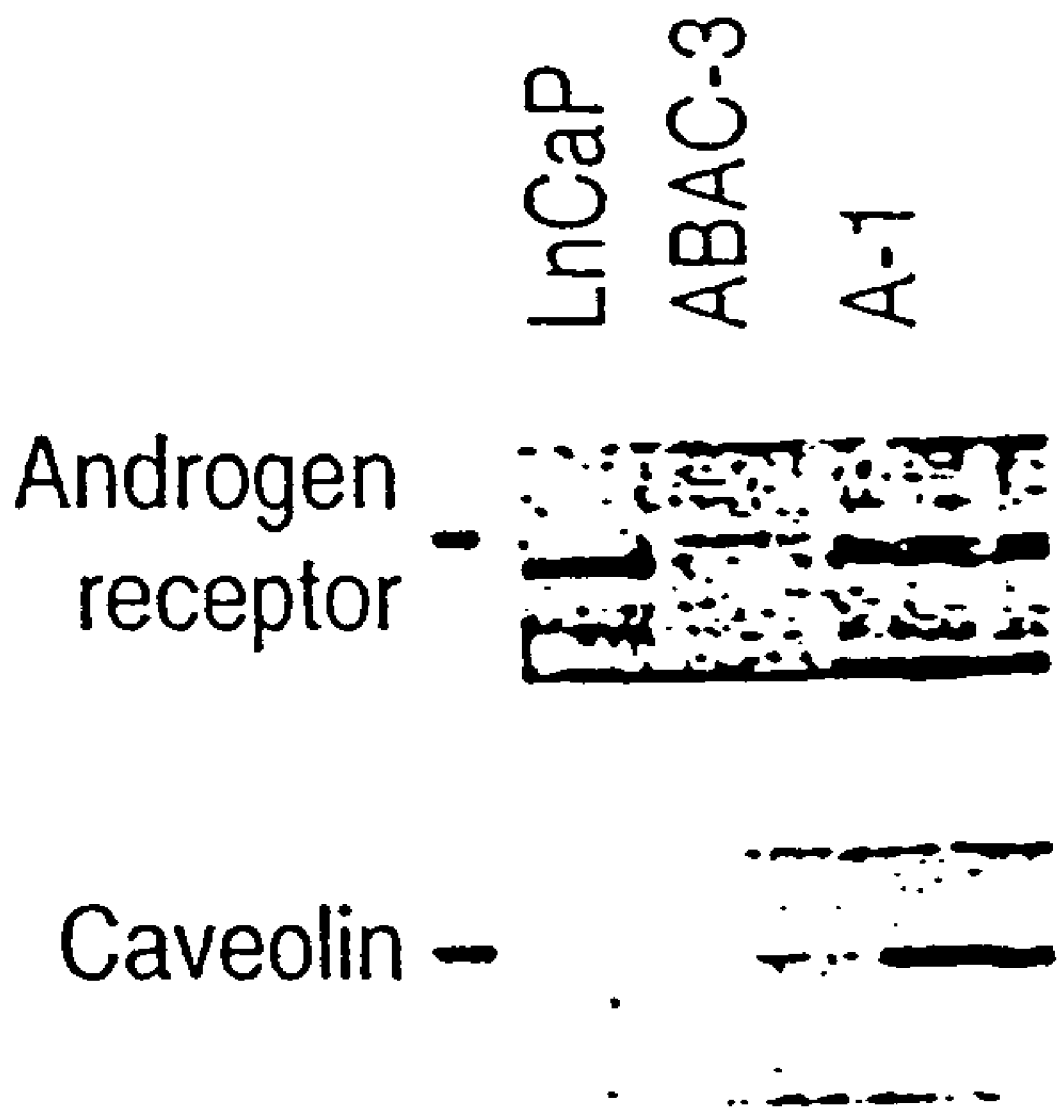
FIG. 2 Western blot of cells grown from three independent injections for one round of ABAC3 orthotopic tumors grown in castrated mice.

As depicted in FIG. 2, preliminary studies indicate increased caveolin as well as AR levels accompany in an androgen-depleted environment in vivo after one round of growth in a castrated host. Specifically, FIG. 2 is a Western blot of cells grown from three independent injections (A-C) for one round of ABAC3 orthotopic tumors grown in castrated animals. Equivalent amounts of protein extract were electrophoresed, transferred to nitrocellulose, and reacted with antibody against androgen receptor (top) or caveolin (bottom). Control LnCaP and ABAC3 cell extracts showed minimal caveolin protein but the ABAC3 cells re-acquired expression of caveolin after passage in the castrated mice. Expression of androgen receptor was also increased by growth in castrated animals.

To reverse the phenotype in a different fashion, all three cell lines (ABAC3, ABAC5, and BACS4) are also used in experiments in which the caveolin (sense) gene is supertransfected using the pBABE-puro expression vector. Selected clones are tested for caveolin protein by immunoblotting, and those that have reacquired expression of caveolin are tested for androgen sensitivity by the assay described above.

Figure 3:
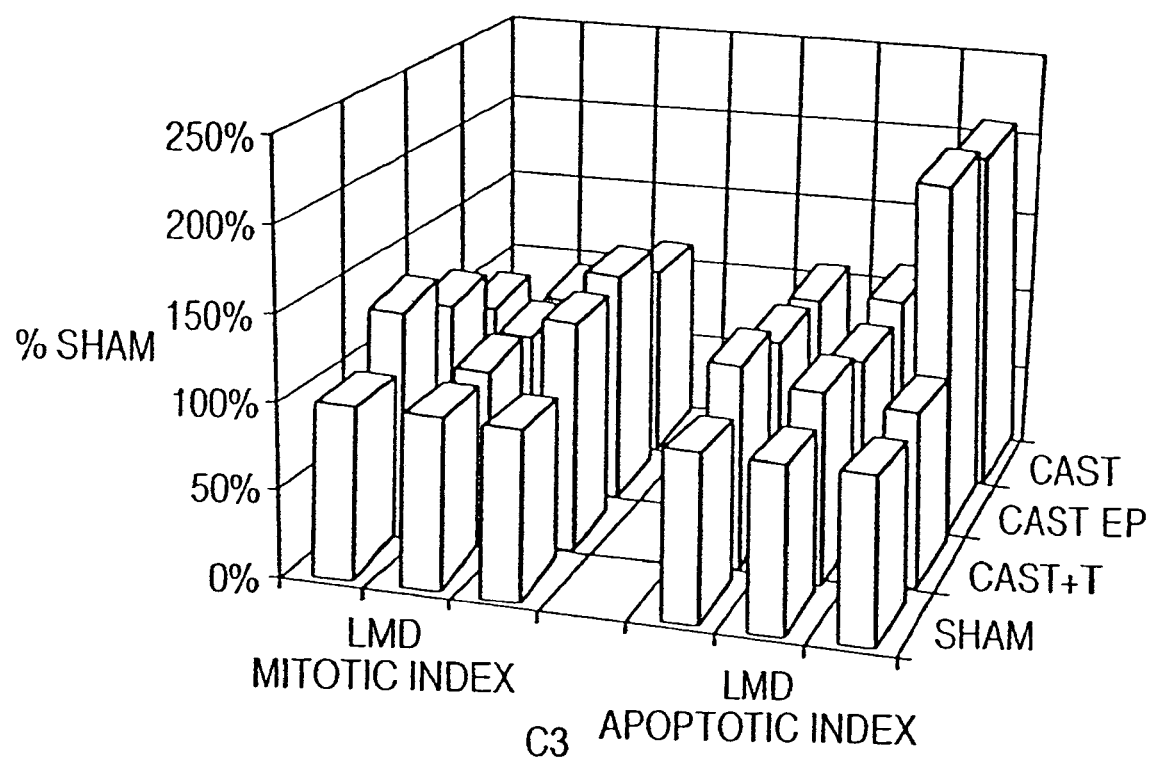
FIG. 3 Graphic depicting increased apoptosis in antisense caveolin tumors in castrated hosts.

In addition, the kinetics of castration-induced regression in all eight cell clones that have been tested for tumorigenicity and hormone sensitivity in vivo are analyzed. Tissues are currently available for these studies such as frozen tissue from previous experiments (see FIG. 1), as well as obtained formalin-fixed blocks for sectioning and H&E staining. To establish the kinetics of cell proliferation, the mitotic index is assessed by counting mitotic figures as well as apoptotic index by the TUNEL method. Aihara M, et al., *Cancer* 75:522-529, 1995; Yang G, et al., *Cancer* 78:1267-1271, 1996; Gavrielli Y, et al., *J. Cell. Biol.* 119:493-501, 1992. As depicted in FIG. 3, these analyses have been performed for one pair of clones with interesting results. Specifically, FIG. 3 depicts the increased apoptosis but not mitosis in antisense caveolin tumors in castrated hosts. Tumors described in FIG. 1 were evaluated for apoptotic index using the TUNEL technique (Gavrielli Y, et al., *J. Cell. Biol.* 119:493-501, 1992) and mitotic index by visually counting mitotic figures.

Frozen tissues are also used to prepare sections for in situ hybridization and to prepare RNA for Northern blotting of selected hormone-responsive genes that have been previously identified in the prostate. These gene activities include c-myc, tPA, uPA, AR, cyclin-D, transglutaminase, TRPM-2 and transforming growth factor-$\beta$1. (Egawa S, et al., *Mol. Carcinog.* 5:52-61, 1991). These analyses are performed on parent cell lines, vector control clones, and antisense caveolin clones to assess the fundamental molecular pathways of the castration-induced pathways based on currently available information.

In regard to the mechanism of action for castration-induced regression and its suppression by overexpression of caveolin, it is believed that nitric oxide synthase (NOS) and nitric oxide production may play a role in this process. These concepts are derived primarily from previous work in both prostate as well as other systems. (Chamness S L, et al., *Fertil. Steril.* 63:1101-1107, 1995). Caveolin may sequester NOS and prevent it from being activated by an undetermined gene activity (possibly calmodulin) (Michel J B, et al., *J. Biol. Chem.* 272:15583-15586, 1997) that is active in parallel with increased calcium influx. To test the fundamental principles of this concept, immunohistochemical staining is performed on tissue sections, as described above, for three forms of NOS, including the inducible form (iNOS), which is believed to be involved. In addition, nitric oxide (NO) production in frozen tissues is measured using an established method. (arginine to citrulline conversion technique) (Wang W, et al., *Anal. Biochem.* 227:274-280, 1995; Hon W M, et al., *Biotechnic & Histochemistry* 72:29-32, 1997). Finally, the sensitivity of this pathway in vivo (and in vitro) is tested using the immunophilin FK506 which has been shown in other tissue systems to inhibit nitric oxide production through interaction by suppressing calmodulin-NOS interactions. (Synder S H, et al., *Nature Medicine* 1:32-337, 1995.) This is performed initially in ABAC3 cells under the hormone conditions specified above.

Many of the gene activities involved in the castration-induced regression pathway have not been previously identified, specifically those that are rate-limiting. The identification of these genes may be pursued using differential display-polymerase chain reaction (DD-PCR) methods. Frozen tissues that have been collected from previous experiments may be used (see FIG. 1). mRNAs are prepared and subjected to differential display using a series of arbitrary ten mers (Yang, G. et al., *Clin. Can. R.* 4:1873-1880, 1998; Ralph D, et al., *Proc. Natl. Acad. Sci. USA* 90:10710-10714, 1993) and DD-PCR fragments are selected based on their differences between vector control clones and antisense caveolin clones, as well as their possible similarities and/or dissimilarities from control tissues that preferably include anterior prostate, ventral prostate, dorsal prostate, and lateral prostate from normal male animals subjected to a similar hormone manipulation as tumors.

Figure 4:
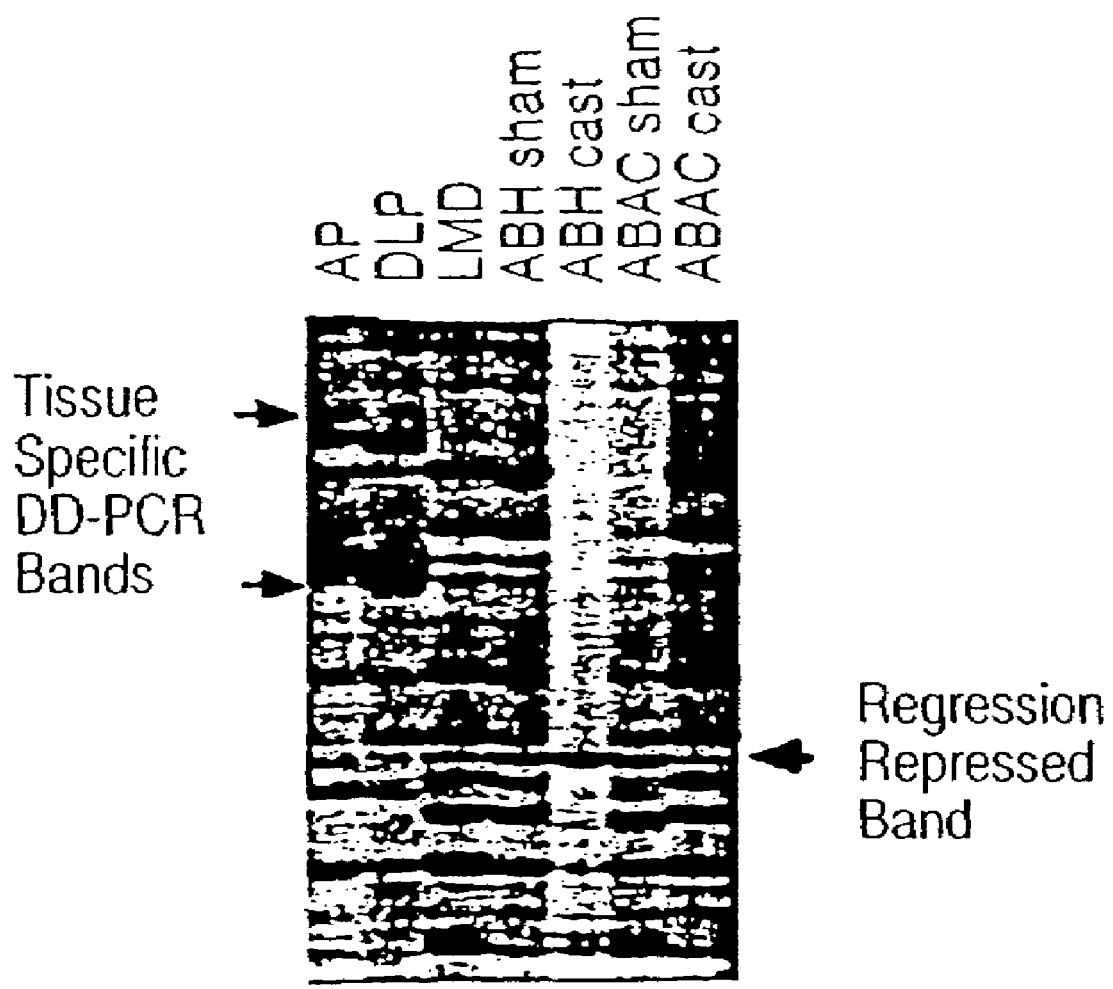
FIG. 4 Preliminary DD-PCR analysis with, mRNA isolated from orthotopic tumor tissue in sham or castrated mice.

FIG. 4 shows a preliminary DD-PCR analysis with mRNA isolated from orthotopic tumor tissue in sham or castrated mice. Control mRNA from normal 129 mouse anterior prostate (AP) or dorsal lateral prostate (DLP) indicates the ability to detect tissue specific gene expression. Repression of a specific band was identified when comparing antisense caveolin clone ABAC3 in the castrated host with the sham host. This same band was present in both sham and castrated mice with the control clone ABH11 or parental LMD tumors. This analysis revealed both tissue specific and castration-induced regression specific bands.

Once identified, these genes are validated for expression in vivo by northern blotting as well as by in situ hybridization. In situ hybridization with sensitive detection methods is critical to localize gene activities to specific cell types in vivo. It is conceivable that cells other than the cancer cells per se play a role in the castration induced regression response. After genes are validated for expression in vivo they are cloned into appropriate expression vectors and tested appropriately in vivo and possibly in vitro, depending on their suspected activity. One possible test is the generation of stable sense and/or antisense clones and their use in the in vivo sensitivity tests.

In addition, in vitro model systems are established for both mouse and human cell lines. All eight mouse prostate cancer cell lines that include parental cell lines, vector control clones, and antisense caveolin clones are compared under conditions of testosterone stimulation and testosterone-free conditions according to previous methods. A panel of three human prostate cancer cell lines that have been stably transfected with vector control as well as antisense or sense caveolin are established, depending on caveolin expression. These cell lines are identified as ND-1 and PC-3 (high caveolin expression) and LNCaP (low to undetectable caveolin). These cells are transfected with expression vectors (containing the neomycin resistance gene) for sense caveolin (LNCaP cells) or antisense caveolin (ND-1 and PC-3 cells) and control vectors (ND-1, PC-3 and LNCaP), and neomycin-resistant clones are selected and characterized for caveolin expression by Western blotting. This further establishes and expands the repertoire of model systems for future studies.

Example 3

Development of Transgenic Mice with Overexpression of Caveolin

Transgenic mice are generated in which overexpression of caveolin is targeted to the prostate gland. Analysis of these mice is undertaken to determine the extent of developmental abnormalities and pathological changes that occur. Hormone manipulation of these mice allows study of prostatic growth and morphogenesis. The mice are also useful for therapeutic studies in vivo.

Figure 5:
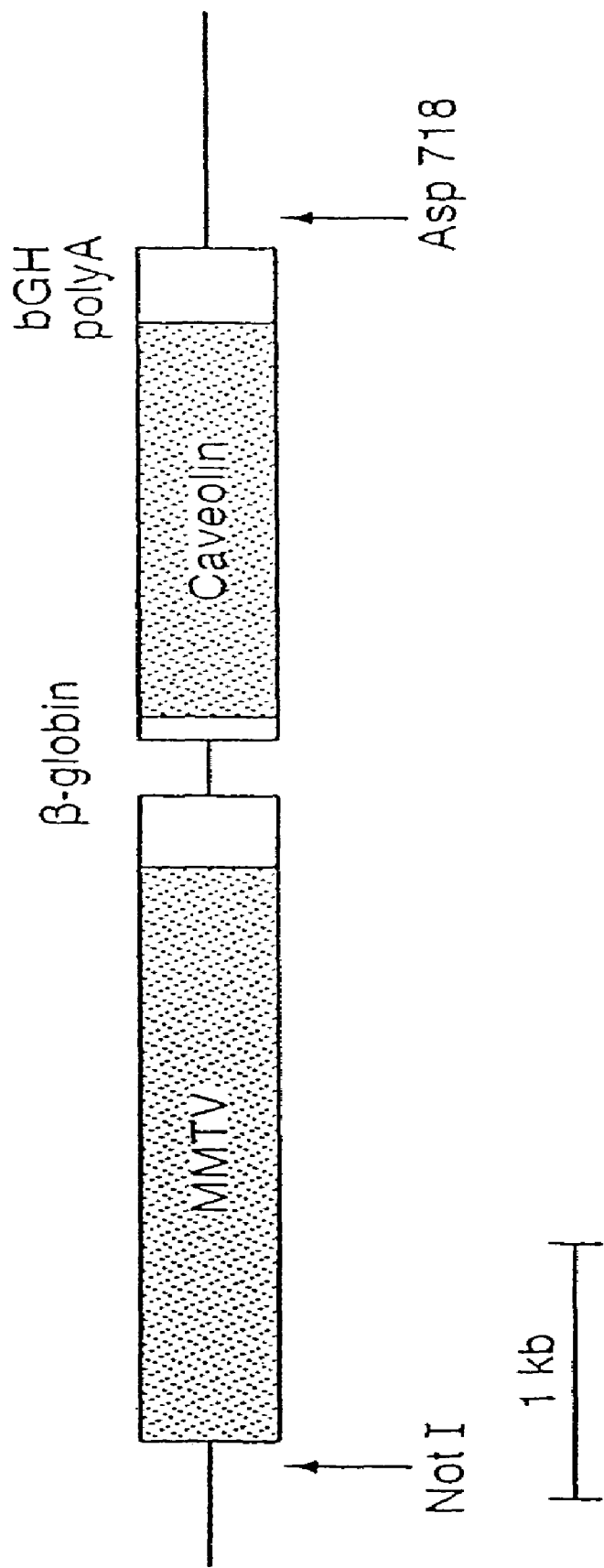
FIG. 5 Construct used for the generation of transgenic mice.

ICR mice have been constructed and injected with the MMTV-caveolin transgene FIG. 5 depicts the construct used for generation of transgenic mice. The human caveolin cDNA was cloned from human prostate mRNA by PCR amplification and sequenced in both directions to confirm the absence of mutations. It was then inserted into pKCR which was specifically chosen to facilitate cDNA transgene expression due to the presence of sequences for the $\beta$-globin spice donor and acceptor and bovine growth hormone poly-adenylation. Expression in this vector is driven by the MMTV promoter which is known to express in hormonally regulated tissues such as the prostate. A NotI to Asp718 fragment was excised from the vector and used for microinjection.

Founder mice are identified as litters become available. The methods involved in identification of founder mice include the analysis of tail DNA using standard PCR-based methodologies established by Dr. Franco DeMayo. Once a founder mouse is identified, it is used to build a colony for further studies. Additional founder mice may be produced in the 129 strain of mice for focmparative analyses. Initial studies using the original founder colony include a close examination of the prostatic tissues and genitourinary system (as well as other organ systems) in order to identify potential developmental abnormalities. Following documentation of any abnormalities, the developmental abnormalities are compared to known pathological abnormalities in both the transgenic mouse system as well as in human prostate. These studies involve both morphological and immnunohistochemical analysis of disease markers (e.g., TGF-β1). The growth and morphology of the breast tissues from non-transgenic and transgenic animals may be compared for abnormalities. This is made possible by the initial selection of the MMTV promoter that is active in both prostate and breast tissues. Comparative studies with breast tissues in this system may extend the understanding of caveolin activities in the prostate as it has in previous experiments. (Yang, G. et al., Clin. Can. R. 4:1873-1880, 1998). Further studies on this mouse involve hormone manipulation using methods which include sham surgery, surgical castration, surgical castration plus TP pellet, and surgical castration plus empty pellet in order to determine the androgen responsiveness of the transgenic prostate tissues. Depending on levels of transgenic caveolin expressed, this model system is not expected to be dependent on androgenic steroids and produce abnormal structures that are not responsive to surgical castration and, accordingly, do not regress.

Example 4

Molecular Reduction of Caveolin

Androgen ablation therapy may be potentiated by molecular reduction of caveolin protein using adenoviral vector systems, antisense oligonucleotides, antisense retroviral vectors, and potentially small molecules and antibodies. Following the direct testing of these therapeutic approaches for reduction of caveolin protein levels in vitro and in vivo, optimal methodologies are selected for the coupling of these therapies with surgical castration in an attempt to produce more widespread cell death in mouse prostate cancer.

Figure 6:
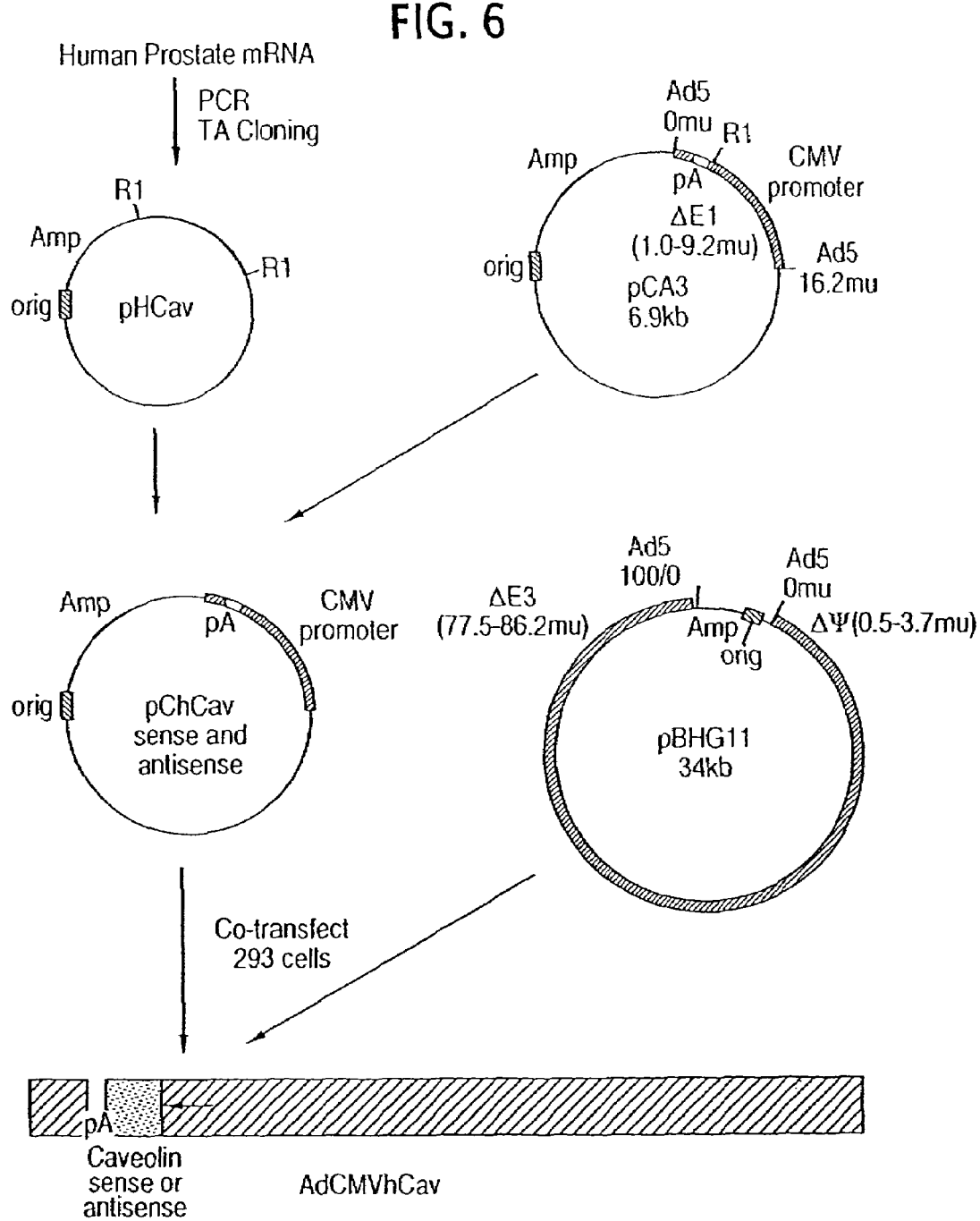
FIG. 6 Schematic of adenovirus construction for CMV-promoter driven human caveolin adenovirus.

The potential therapeutic applicability of restoring androgen sensitivity through reduced caveolin expression is explored through a series of gene-based approaches. Adenoviral vectors are constructed, which transduce both sense and antisense mouse and human caveolin using technologies established in the laboratory (see FIG. 6). In general, this approach involves the subcloning of full-length cDNA fragments into pCA3 (a CMV promoter-driven shuttle vector) and pAD-12 (an RSV promoter-driven shuttle vector). For both mouse and human constructs, both kinds of vectors are produced, as one promoter system may be preferred over the other due to its increased cell-specific activities. These shuttle vectors are co-transfected with a second-generation vector plasmid (pBHG11), and recombinant viruses are identified using established assay technologies. Following purification and characterization of the viruses in vitro for fundamental performance parameters, they are tested for efficacy initially using in vivo systems and subsequently in in vitro systems. The in-vivo systems involve those as stated in Example 2and involve inoculation of parental cell lines and vector control clones into normal male adult animals. Following 3 days' growth, adenoviral vectors containing sense and antisense caveolin are infected into the tissue (approximately $10^8$-$10^9$ total PFUs), and animals are surgically castrated at that time. Some animals are injected with empty vector as a control. Subsequent hormone manipulation is performed on all animals as described in Example 2 and includes sham surgery, surgical castration, surgical castration plus TP pellet, and surgical castration plus empty pellet. For each hormone condition, three vector injections are performed, bringing the total to 12 groups of 8-12 separate tumors per group. Both the, growth potential (wet weight) as well as other biological parameters of castration-induced regression are evaluated, including mitotic index, apoptosis, and gene expression (both northern blotting and in situ hybridization), as described in Example 2, for each surgery/hormone treatment. In addition, depending on the results of these experiments, additional approaches that include antisense oligonucleotides, as well as antisense retroviral vector systems may be pursued.

The present invention will help to provide a molecular model for specific interactions among molecules involved in the castration-induced regression pathway and, therefore, the development of small molecules or possibly antibodies as therapeutic vehicles. Hormone sensitivity in high caveolin expressing mouse and human prostate cancer cells will be produced by reducing caveolin levels with overexpression of antisense caveolin as transduced with recombinant adenoviral vectors. Caveolin levels have already been suppressed in the stable antisense caveolin clones that established the initial model system of the present invention.

Other embodiments and uses of the invention will be apparent to those skilled in the art from consideration of the specification and practice, of the invention disclosed herein. All documents cited herein including U.S. Pat. No. 5,783,182 entitled "Method for Identifying Metastatic Sequences," which issued Jul. 21, 1998, are specifically incorporated by reference. The specification and examples should be considered exemplary only with the true scope and spirit of the invention indicated by the following claims.

I claim:

1. A method for treating a subject having a prostatic malignant neoplasm comprising administering to the subject a composition comprising an anti-caveolin antibody wherein the antibody is effective to inhibit metastasis in the neoplasm.

2. The method of claim 1, wherein the neoplasm is hormone responsive.

3. A method for treating a neoplastic disease of the prostate comprising administering to a subject in need thereof an anti-caveolin agent in conjunction with androgen ablation therapy.

4. The method of claim 3, wherein the anti-caveolin agent is an anti-caveolin antibody.

5. The method of claim 4, wherein the antibody is a monoclonal antibody.

6. The method of claim 4, wherein the antibody is a polyclonal antibody.

7. The method of claim 3, wherein the androgen ablation therapy comprises administration of a composition comprising an anti-androgen antibody to the subject.

* * * * *